United States Patent
Xi et al.

(10) Patent No.: US 9,610,447 B2
(45) Date of Patent: Apr. 4, 2017

(54) SYSTEMS AND METHODS FOR SELECTING PACING VECTORS BASED ON SITE OF LATEST ACTIVATION FOR USE WITH IMPLANTABLE CARDIAC RHYTHM MANAGEMENT DEVICES

(75) Inventors: Cecilia Qin Xi, San Jose, CA (US); Diana Gavales, Pasadena, CA (US); Andrew Miller, Redondo Beach, CA (US); Andrew W. McGarvey, Los Angeles, CA (US); Zachary Briggs, Palm Springs, CA (US); David Bishop, Napa, CA (US); Sharon Standage, Leona Valley, CA (US); Anil Keni, Los Angeles, CA (US); Richard Block, Valencia, CA (US); Heidi Hellman, Los Angeles, CA (US); Taryn Smith, Placerville, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 17 days.

(21) Appl. No.: 13/436,578

(22) Filed: Mar. 30, 2012

(65) Prior Publication Data
US 2013/0261687 A1 Oct. 3, 2013

(51) Int. Cl.
*A61N 1/36* (2006.01)
*A61N 1/368* (2006.01)

(52) U.S. Cl.
CPC .................................. *A61N 1/3686* (2013.01)

(58) Field of Classification Search
CPC .. A61N 1/3627; A61N 1/0416; A61N 1/3684; A61N 1/36585; A61N 1/3682; A61N 1/368; A61N 1/3987; A61N 1/3686

USPC .......................................................... 607/18
See application file for complete search history.

(56) References Cited

U.S. PATENT DOCUMENTS

| | | | |
|---|---|---|---|
| 5,833,623 A | 11/1998 | Mann et al. | 600/523 |
| 6,477,406 B1 | 11/2002 | Turcott | 600/518 |
| 6,512,952 B2 | 1/2003 | Stahmann et al. | 607/9 |
| 6,628,988 B2 | 9/2003 | Kramer et al. | 607/9 |
| 6,643,546 B2 | 11/2003 | Mathis et al. | 607/9 |
| 6,772,008 B2 | 8/2004 | Zhu et al. | 607/9 |
| 7,248,925 B2 | 7/2007 | Bruhns et al. | 607/25 |
| 7,299,093 B2 | 11/2007 | Zhu et al. | 607/9 |
| 7,590,446 B1 | 9/2009 | Min et al. | 607/9 |
| 7,787,951 B1 | 8/2010 | Min | 607/17 |

(Continued)

*Primary Examiner* — Michael Kahelin
*Assistant Examiner* — Minh Duc Pham
(74) *Attorney, Agent, or Firm* — Theresa A. Raymer

(57) ABSTRACT

Techniques are provided for use with an implantable cardiac stimulation device equipped with a multi-pole left ventricular (LV) lead and a right ventricular (RV) lead for identifying suitable pacing vectors. In one example, RV-LV delay times are measured while using different electrodes of the LV lead as cathodes for sensing. The LV electrode having the longest RV-LV delay time is identified and LV capture thresholds and diaphragmatic stimulation thresholds are measured for pacing vectors that employ that LV electrode as a cathode. Assuming at least one vector employing the selected LV electrode is found to have acceptable thresholds, the vector is selected for use in delivering pacing therapy with the selected LV electrode. If none of the pacing vectors employing the selected LV electrode has acceptable thresholds, another LV electrode is selected and the procedure is repeated. Examples with a multi-pole RV lead are also described.

18 Claims, 15 Drawing Sheets

(56) References Cited

U.S. PATENT DOCUMENTS

| | | | |
|---|---|---|---|
| 7,881,787 B1 | 2/2011 | Min | 607/9 |
| 7,881,810 B1 | 2/2011 | Chitre et al. | 607/129 |
| 7,899,536 B1 | 3/2011 | Hellman | 607/27 |
| 7,917,194 B1 | 3/2011 | Reed et al. | 600/509 |
| 7,917,214 B1 | 3/2011 | Gill et al. | 607/9 |
| 2002/0177879 A1 | 11/2002 | Ding et al. | 607/9 |
| 2005/0125041 A1 | 6/2005 | Min et al. | 607/9 |
| 2007/0179390 A1 | 8/2007 | Schecter | 600/508 |
| 2008/0306567 A1 | 12/2008 | Park et al. | 607/27 |
| 2009/0299423 A1 | 12/2009 | Min | 607/9 |
| 2010/0042176 A1 | 2/2010 | Snell | 607/28 |
| 2010/0100148 A1 | 4/2010 | Min et al. | 607/27 |
| 2010/0145405 A1 | 6/2010 | Min et al. | 607/25 |
| 2010/0262204 A1* | 10/2010 | McCabe | A61N 1/3627 607/17 |
| 2011/0004264 A1* | 1/2011 | Siejko | A61N 1/371 607/28 |
| 2011/0022106 A1 | 1/2011 | Min | 607/14 |
| 2011/0022110 A1 | 1/2011 | Min | 607/25 |
| 2011/0022112 A1 | 1/2011 | Min | 607/25 |
| 2011/0066203 A1 | 3/2011 | Rosenberg et al. | 607/17 |
| 2011/0098772 A1* | 4/2011 | Min | A61N 1/36185 607/28 |
| 2011/0184274 A1 | 7/2011 | Rosenberg et al. | 600/424 |
| 2011/0213260 A1 | 9/2011 | Keel et al. | 600/513 |
| 2011/0319951 A1 | 12/2011 | More et al. | 607/14 |
| 2011/0319953 A1 | 12/2011 | Reed et al. | 607/14 |

* cited by examiner

SYSTEMS AND METHODS FOR SELECTING PACING VECTORS BASED ON SITE OF LATEST ACTIVATION FOR USE WITH IMPLANTABLE CARDIAC RHYTHM MANAGEMENT DEVICES

FIELD OF THE INVENTION

The invention relates to implantable cardiac rhythm management devices (CRMDs) such as cardiac resynchronization therapy (CRT) devices or implantable cardioverter-defibrillators (ICDs) and, in particular, to techniques for selecting pacing vectors for use with CRT.

BACKGROUND OF THE INVENTION

CRT device implant can be challenging, for example, when the left ventricular (LV) lead is placed intravenously, advancing through the coronary sinus (CS) and into a selected branch of the cardiac venous system. It can be difficult to find an optimal location for placement of the lead due to patient variability in venous anatomy. A further challenge, after lead implant, is that positional changes may cause the lead to be micro-dislodged or even migrated. This may result in a decrease of the diaphragmatic stimulation threshold (i.e. the threshold above which a stimulation pulse delivered using the lead inadvertently triggers contraction of diaphragmatic muscles) and/or an increase of the LV capture threshold (i.e. a threshold above which a stimulation pulse properly triggers contraction of LV myocardial tissues.) LV pacing pulses should be set with a pulse magnitude above the LV capture threshold and yet below the diaphragmatic threshold. If lead migration causes the diaphragmatic stimulation threshold to decrease, then an LV pacing pulse initially set to avoid inadvertent stimulation of the diaphragm may nevertheless result in such stimulation. Likewise, if lead migration or other factors cause the LV capture threshold to increase, then an LV pacing pulse initially set to a pulse magnitude sufficient to depolarize the LV may fail to do so. Still further, thresholds may change once the patient becomes ambulatory following device implant.

State-of-the-art multi-electrode LV leads for use with CRT (such as St. Jude Medical's quadripolar Quartet™ lead) allow for "electronic repositioning", i.e. the lead provides a set of electrodes for implant at different locations along the LV that can be independently selected for use in delivering pacing pulses so as to help avoid diaphragmatic stimulation while ensuring LV capture. For example, if the most distal of the LV electrodes (i.e. the LV tip electrode) is initially used for delivering pacing pulses to the LV but lead migration eventually causes those pulses to also trigger diaphragmatic stimulation, then another one of the electrodes of the LV lead (at a more proximal location) can instead be selected for delivering LV stimulation. In general, any combination of the LV electrodes may be selected—in conjunction with right ventricular (RV) lead electrodes or other electrodes— to define one or more pacing vectors for delivery of stimulation. In this manner, lead migration problems can be addressed through electronic repositioning (in combination with any needed adjustments to the pulse magnitude or other programmable pacing parameters) so as to deliver LV pacing above the LV capture threshold while avoiding diaphragmatic stimulation. Electronic repositioning can save implant time as well as reduce the need for post-operative lead re-intervention. In practice, a clinician uses an external programmer to control the implanted CRT device to perform various capture threshold tests using various combinations of pacing vectors to identify a suitable pacing vector to ensure LV capture without diaphragmatic stimulation.

Electronic repositioning is discussed, for example, U.S. Patent Application 2011/0213260 of Keel et at, entitled "CRT Lead Placement based on Optimal Branch Selection and Optimal Site Selection"; U.S. Patent Application 2011/0184274 entitled Rosenberg et al., entitled "Electrode Configurations for Leads or Catheters to Enhance Localization using a Localization System"; U.S. Patent Application 2011/0066203 of Rosenberg et al., entitled "Electrode and Lead Stability Indexes and Stability Maps based on Localization System Data" and U.S. Pat. No. 7,917,194 to Reed et al., entitled "Method and Apparatus for Detecting Pulmonary Edema."

However, a quadripolar LV lead offers numerous programmable pacing/sensing vectors and so testing the capture thresholds and diaphragmatic stimulation thresholds for the entire set of programmable vectors can be complicated and time consuming. In particular, the workflow that a clinician typically must go through to perform and manage the various tests to identify suitable pacing vectors can be complex and time consuming. A multi-electrode lead with more electrodes would present an even greater number of vectors. A quicker, easier and more systematic method for testing and documenting suitable vector or vectors is desirable to facilitate lead positioning and vector selection and to simplify clinician workflow. It is to this end that aspects of the invention are generally directed.

SUMMARY OF THE INVENTION

In an exemplary embodiment, a method is provided for use with an implantable CRT device (or other suitable implantable medical device) for identifying suitable pacing vectors for use with multi-pole LV leads. Briefly, RV-LV delay times are measured while using different electrodes of the LV lead as sensing cathodes to measure an RV-LV delay time for each LV electrode. An LV electrode is selected based on the measured RV-LV delay times, such as by selecting the LV electrode having the longest RV-LV delay time (i.e. the LV electrode located at the site of latest activation (SOLA.)) Stimulation thresholds are measured for pacing vectors that employ the selected LV electrode, such as LV capture thresholds or diaphragmatic stimulation thresholds, or both. Assuming that at least one vector employing the selected LV electrode is found to have an acceptable threshold, that vector is identified and selected for use in delivering pacing therapy with the selected LV electrode as a cathode. If none of the vectors employing the selected LV electrode has an acceptable threshold, then another LV electrode such as the electrode with the next longest RV-LV delay is selected and the procedure is repeated. In this manner, an expedited test procedure is provided wherein only a subset of the total number of possible pacing vectors is initially tested to identify acceptable pacing vectors, thereby reducing the amount of time and effort needed to identify suitable vectors and, in particular, simplifying clinician workflow. The technique exploits the use of LV electrodes as cathodes because it is believed that the cathode has a more important role in determining pacing efficacy than the anode. The expedited procedure, which may be referred to as Site Optimization (SiteOpt), is typically performed by a programmer under the supervision of a clinician. The programmer transmits suitable control signals to the CRT device, which performs the RV-LV delay time tests and capture threshold tests. However, if suitably equipped, the CRT device itself may perform the procedure independent of the programmer so as to automatically take advantage of electronic repositioning, where appropriate. This technique, which exploits a multi-pole LV lead, is particularly advantageous for use within patients with left bundle branch block (LBBB) where the SOLA is located in the LV. For patients where the SOLA is instead located in the RV (such as patients with right bundle branch block (RBBB)), an alternative procedure that exploits a multi-pole RV lead may be used. The multi-pole LV lead example is the primary example described herein since most heart failure patients have LBBB.

In a first illustrative implementation, the procedure is controlled by an external programmer in communication with an implantable CRT device equipped with a bipolar RV lead and a quadripolar LV lead. Under clinician supervision and control, the external programmer sends signals to the CRT device to control the CRT device to measure RV-LV delay times for each of the four electrodes of the LV lead as sensing cathodes (e.g. LV tip-RV, LV Mid 2-RV, LV Mid 3-RV and LV Prox 4-RV.) In one example, the RV coil electrode is used as the anode during sensing. Delay time tests may be performed either for paced RV events (RV pace) or for intrinsic RV events (RV sense) based on clinician selection. For RV pace, the pacing vector may be, e.g., RV tip to RV ring and the measured delay is the time interval between delivery of the RV pulse and detection of a subsequent LV sensed event. For RV sense, the measured delay is the time interval between an RV sense and an LV sense (which might be negative if LV depolarizes before the RV.) The CRT device then relays the measured RV-LV delay times to the external programmer, which identifies the LV electrode having the longest delay time, i.e. the LV electrode corresponding to the SOLA. The programmer then sends signals to the CRT device to control the CRT device to perform LV capture threshold tests and diaphragmatic stimulation threshold tests to determine whether at least one of the pacing vectors using the selected LV electrode as a cathode has a suitable LV capture threshold and a suitable diaphragmatic stimulation threshold. This may be performed by delivering test pacing pulses of differing magnitudes to the heart using the various vectors while checking to verify that the pulses succeed in evoking LV capture but do not inadvertently trigger diaphragmatic stimulation. LV capture may be verified based on an examination of the LV intracardiac electrogram (IEGM). Diaphragmatic contractions may be detected using accelerometers or other suitable sensors or by direct observation of the patient by the clinician. Typically, the programmer verifies LV capture based on IEGM signals received from the implanted device, though in some examples the implanted device itself might verify LV capture and then send suitable test result signals to the programmer for clinician review. Likewise, in some examples, the implanted device detects diaphragmatic capture based on accelerometer signals and sends suitable test result signals to the programmer for clinician review.

Assuming that one or more of the pacing vectors being tested passes the LV capture test while avoiding diaphragmatic stimulation, the acceptable vectors are identified by the external programmer as candidate vectors for presentation to the clinician via a display screen of the programmer, along with suitable diagnostic data such as the pulse magnitudes used during the tests and the resulting IEGMs. If none of the initial set of vectors passes the tests, a different LV electrode is selected and the tests are repeated with a different set of vectors until at least one suitable candidate vector is identified. The clinician can then chose to program the CRT device to use one of the candidate vectors or can select different vectors to be tested by, for example, selecting yet another one of the LV electrodes. Hence, the clinician retains the flexibility to program the CRT device using whichever vector the clinician deems appropriate, but the use of the LV cathode electrode corresponding to the SOLA as a basis for initially selecting a subset of vectors for testing can expedite the overall test procedure to thereby reduce the amount of time and effort needed to identify suitable vectors.

In a second illustrative implementation, the procedure is performed by the implantable CRT device itself, perhaps in response to a persistent loss of capture (LOC) in the LV occurring while using its currently programmed pacing vector, as might occur due to lead displacement or migration. In this implementation, assuming the CRT device is suitably equipped and programmed, the CRT device automatically performs the series of tests to measure RV-LV delay times for the four electrodes of the LV lead (while using the LV electrodes as cathodes for sensing.) Again, RV-LV delay time tests can be performed either for paced RV method or for intrinsic RV method. The CRT device analyzes the measured RV-LV delay times to identify the LV electrode experiencing the longest RV-LV delay. The CRT device then performs LV capture threshold tests and diaphragmatic stimulation threshold tests to identify an LV pacing vector incorporating the selected LV cathode electrode that has a suitable LV capture threshold and a suitable diaphragmatic stimulation threshold. Assuming that one or more of the vectors being tested passes the LV capture test while avoiding diaphragmatic stimulation, the acceptable vectors are identified by the CRT device and one is selected for use in delivering additional pacing. If none of the initial set of vectors passes the LV capture test while avoiding diaphragmatic stimulation, the tests are repeated using a different LV cathode electrode such as the electrode with the next longest RV-LV delay and a different set of vectors until a suitable pacing vector is found. In this manner, the CRT device can automatically respond to a persistent LOC in the LV by exploiting electronic repositioning to identify a new pacing vector. In any case, pertinent diagnostic data is recorded and warnings can be generated to alert the patient to consult his or her physician, who then reviews the operation of the CRT device and makes further programming adjustments, if warranted.

System and method implementations of these and other techniques are presented herein. Although summarized primarily with respect to implementations having a quadripolar LV lead, aspects of the invention are also generally applicable to systems having other multi-pole LV leads or to systems having multi-pole RV leads. As noted, the use of a multi-pole RV lead would be particularly appropriate for patients where the SOLA is in the RV instead of the LV.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Systems and Methods

Figure 1:
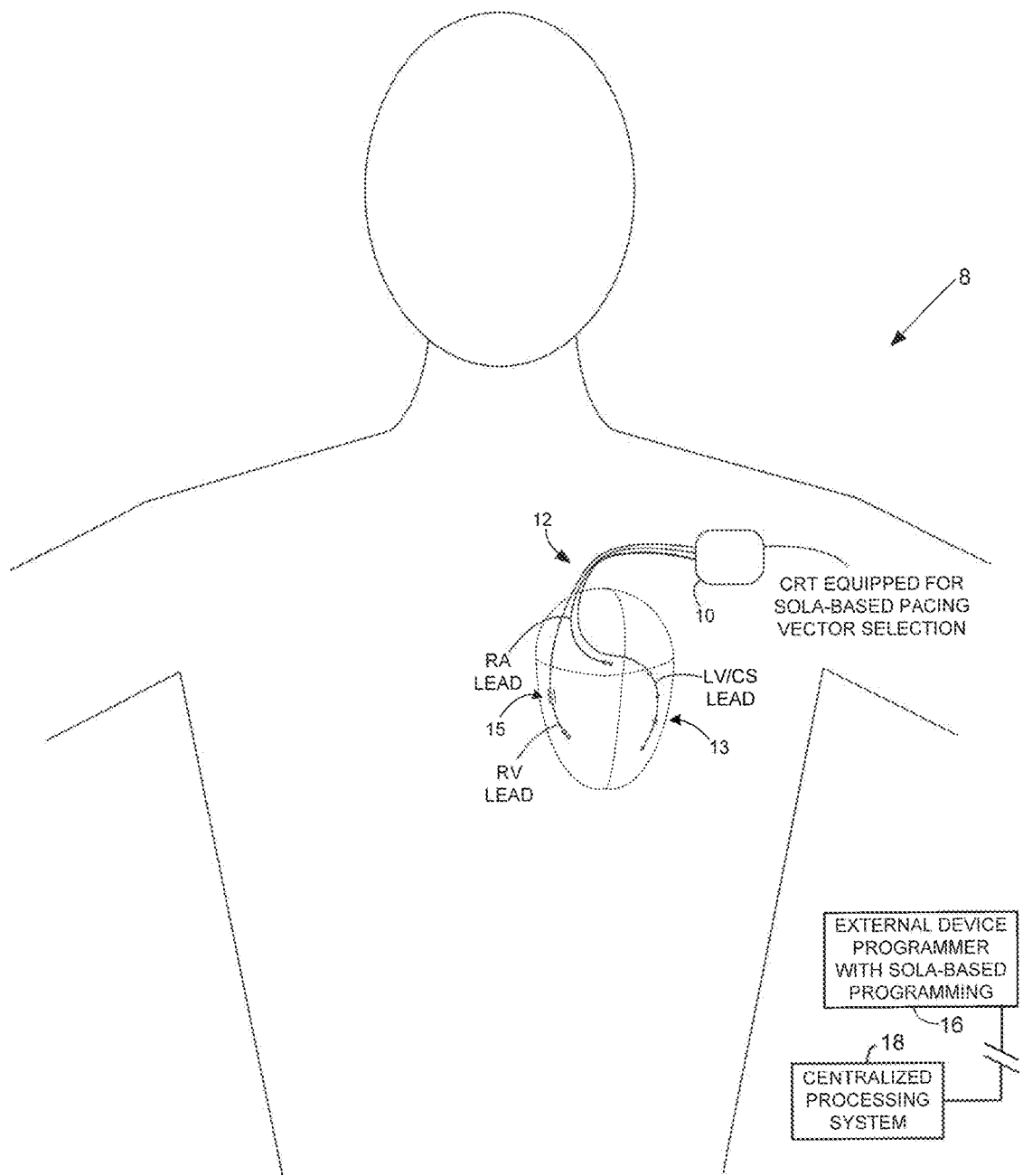
FIG. 1 illustrates components of an implantable medical system having a CRT device (or other suitable CRMD) equipped for SOLA-based pacing vector selection that exploits LV electrodes as cathodes.

FIG. 1 illustrates an implantable medical system 8 equipped for expedited identification of suitable pacing vectors (alone or in conjunction with an external programmer.) In this example, the implantable medical system 8 includes a CRT device 10 (which may be a pacer, ICD, CRT or other suitable device) equipped with a set of cardiac sensing/pacing leads 12 implanted on or within the heart of the patient, including a multi-pole LV lead implanted via the CS. In FIG. 1, a stylized representation of the leads is provided. More accurate illustrations of the leads are provided within the other figures. To illustrate the multi-pole configuration of the LV lead, a set of electrodes 13 is shown distributed along the LV lead. In the examples described herein, a quadripolar lead is employed (such as the Quartet™ lead provided by St Jude Medical.) Other suitable leads may instead be employed, including leads with more or fewer electrodes. Also, as shown, an exemplary RV lead is provided that includes an RV tip/ring electrode pair and an RV coil 15. An RA lead is also shown, which includes an RA tip/ring pair. Other electrodes of various sizes and shapes may be additionally or alternatively provided, such as coil electrodes mounted in the RA or in the CS near the left atrium (LA.) The various leads can be intravenous, pericardial, endocardial or "leadless" LV pacing devices. For pericardial implant techniques, see, for example, U.S. Pat. No. 7,881,810 to Chitre et al., entitled "Cardiac Access Methods and Apparatus."

In some implementations, the CRT device itself performs the expedited vector identification procedure based on IEGM signals sensed using its leads and other parameters detected by implantable physiological sensors such as accelerometers (not specifically shown in FIG. 1.) In other implementations, the device transmits pertinent IEGM signals and other parameters to an external programmer 16, which identifies suitable pacing vectors under the supervision of a clinician or other user. Note that other external systems might instead be employed, such as bedside monitors or the like. In some embodiments, the external system is directly networked with a centralized computing system, such as the HouseCall™ system or the Merline@home/Merlin.Net systems of St. Jude Medical, which can perform at least some of the processing.

Figure 2:
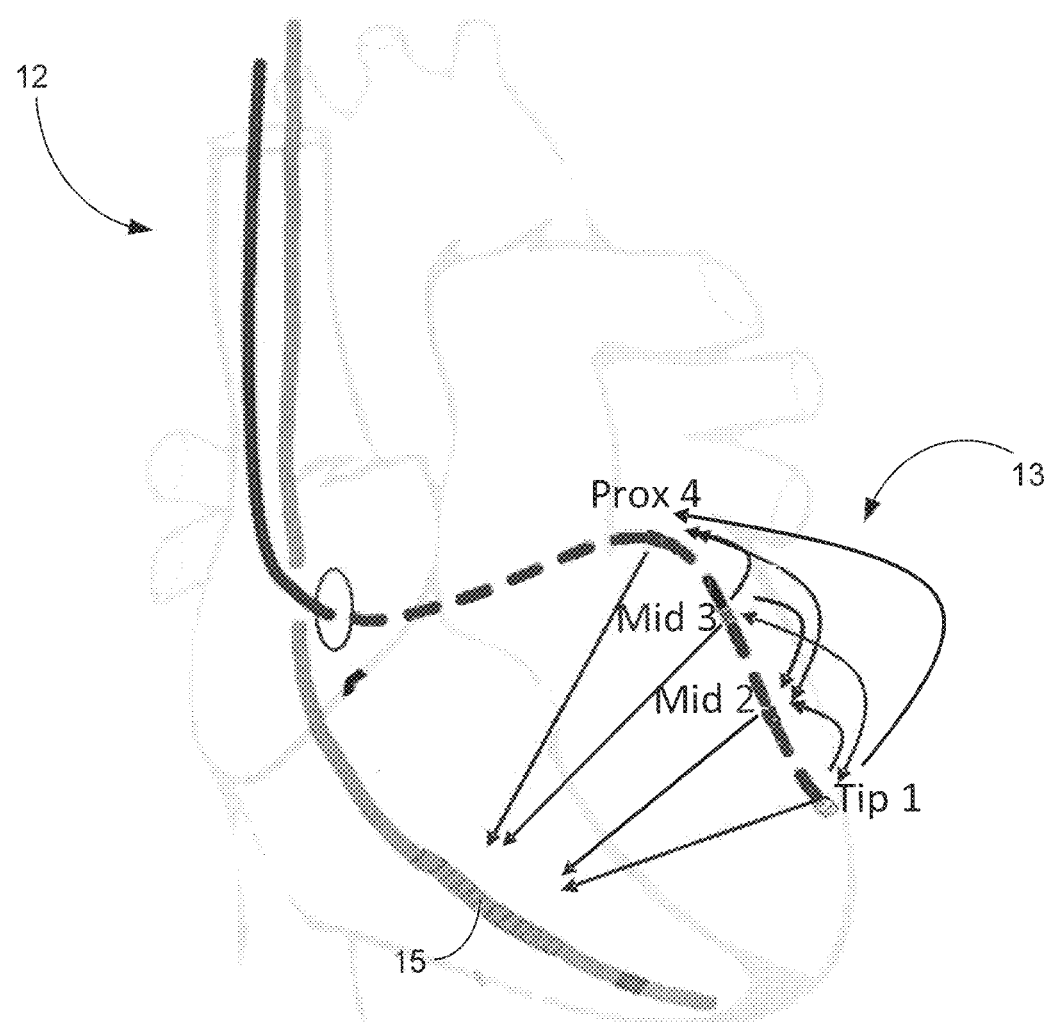
FIG. 2 illustrates a multi-pole LV lead and various exemplary pacing vectors for use with the system of FIG. 1.

FIG. 2 provides another stylized illustration of the heart of the patient showing the RV and LV leads of lead system 12 in greater detail and, in particular, showing the four LV electrodes of the exemplary quadripolar LV lead. The LV electrodes are denoted—from distal LV to proximal LV—as: Tip 1 (or T1), Mid 2 (or M2), Mid 3 (or M3), and Prox 4 (or P4.) The figure also shows various pacing vectors between the LV electrodes and RV coil electrode 15 and further illustrates various LV interelectrode vectors among the electrodes of the LV lead. A total of ten vectors are shown. Note that the particular locations of the implanted components shown in FIGS. 1 and 2 are merely illustrative and might not necessarily correspond to actual implant locations. Also, although the descriptions herein use the Quartet™ lead as an exemplary component of the invention, it should be understood that any suitable LV lead could instead be used.

Figure 3:
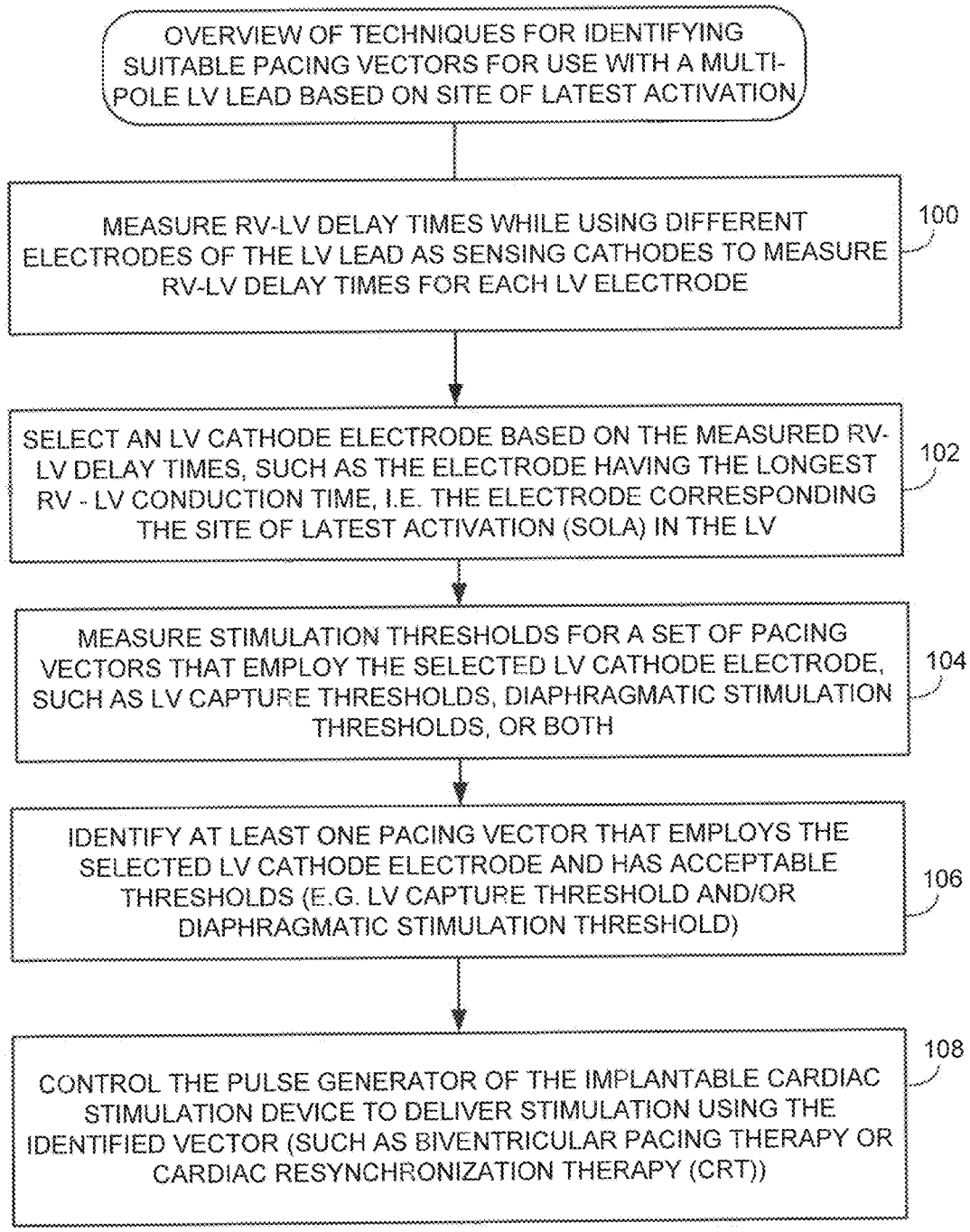
FIG. 3 summarizes a general LV SOLA-based technique for identifying suitable pacing vectors that exploits LV electrodes as cathodes, which may be performed by the system of FIGS. 1 and 2.

FIG. 3 broadly summarizes the expedited techniques exploited by the CRT device of FIG. 1 (or other suitably-equipped systems) for identifying suitable pacing vectors for use with a multi-pole LV lead, especially for use with patients with LBBB where the SOLA is in the LV. Beginning at step 100, RV-LV delay times are measured while using the different electrodes of the LV lead as cathodes for sensing to measure RV-LV delay times for each LV electrode. For example, a set of time delay tests may be performed based on either paced or sensed events in the RV while sensing the LV IEGM to detect resulting interventricular delay times. At step 102, an LV electrode is selected based on the measured RV-LV delays times, preferably the LV electrode having the longest RV-LV delay time (i.e. the electrode having the SOLA.) At step 104, stimulation thresholds are measured for a set of pacing vectors that employ the selected LV cathode electrode. For example, a set of LV capture threshold tests and diaphragmatic stimulation tests may be performed, in which pacing pulses of different magnitudes are delivered for each of the set of vectors while the LV IEGM is analyzed to detect LV evoked responses (i.e. LV capture) and while accelerometer signals are analyzed to detect diaphragmatic stimulation. At step 106, one or more vectors are identified that employ the selected LV electrode and have acceptable thresholds. If none of the vectors tested at step 104 have acceptable thresholds, a different LV cathode electrode can be selected at step 102 and the process repeated until a suitable vector is found. At step 108, the pulse generator of the CRT device is controlled to deliver electrical stimulation using one or more of the vectors found to be suitable. The stimulation may include, e.g., biventricular pacing therapy or CRT. With this technique, suitable pacing vectors are conveniently identified so that CRT pacing can then be delivered relatively close to the SOLA, which in theory, should improve the efficacy of the CRT. Also, within implementations where the clinician manages the procedure using a programmer, the technique serves to simplify clinician workflow by reducing the number of tests that the clinician typically must perform. That is, the procedure conveniently simplifies an otherwise complex set of pacing vector selection tests.

Note that CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for maintaining Synchronized Pacing". See, also, U.S. Patent Application No. 2008/0306567 of Park et al., entitled "System and Method for Improving CRT Response and Identifying Potential Non-Responders to CRT Therapy"; and U.S. Patent Application No. 2007/0179390 of Schecter, entitled "Global Cardiac Performance." See, also, U.S. Patent Application 2011/0319951 of More at al., entitled "Systems and Methods for Use by an Implantable Medical Device for Controlling Multi-Site CRT Pacing in the Presence of Atrial Tachycardia"; and U.S. Patent Application 2011/0319953 of Reed at al., entitled "Systems And Methods For Use By An Implantable Medical Device For Controlling Multi-Site CR Pacing In The Presence Of Atrial Tachycardia."

Hence, systems and methods are provided for programming CRT device electrical stimulation vectors based, at least in part, on the LV cathode electrode corresponding to the SOLA. By initially identifying the LV cathode electrode that represents the SOLA, an expedited test procedure is thereby provided that can reduce the total number of pacing vectors to be tested, thereby reducing the time and effort needed to identify suitable pacing vectors. These techniques will now be described in more detail with reference to various exemplary embodiments.

Exemplary LV SOLA Techniques for Use with an External Programmer

FIGS. 4-9 illustrate an implementation where an external programmer is employed to control the procedure of FIG. 3 for use in programming the CRT device and wherein a quadripolar LV lead is employed. Beginning at step 200 of FIG. 4, the programmer, under the supervision of a clinician, sends controls signals to the CRT device to program the CRT device to measure paced RV-LV delay times for each of the LV electrodes by delivering pacing pulses to the RV and then using the LV electrodes as cathodes to sense LV activation (i.e. the device measures an RV-LV conduction time.) More specifically, for a first one of the electrodes of the LV lead (such as the Tip 1 electrode), the CRT device performs an "RV pace test" wherein pacing pulses are delivered to the RV using the RV tip-RV ring electrodes to trigger RV depolarization and then an LV IEGM is sensed using the particular LV electrode (in this case Tip 1) as a cathode to detect LV activation (while using, e.g., the device "can" as the anode for sensing the IEGM.) The time delay between the RV pulse and the LV activation (the positive or negative peak, the absolute peak, or the max slope etc. can be used as the fiducial point) observed in the LV IEGM is the measured RV-LV delay for that particular LV electrode (Tip 1.) Several pacing pulses may be delivered and the resulting measured RV-LV delays then combined together to yield, e.g., an averaged paced RV-LV delay value for subsequent comparison to other paced RV-LV delays for other LV electrodes. Then, for a second one of the electrodes of the LV lead (such as the Mid 2 electrode), the CRT device performs another RV pace test while the LV IEGM is sensed using the selected LV electrode (in this case Mid 2) as a cathode to detect LV activation. Paced RV-LV delays for that particular electrode (Mid 2) are measured and averaged together. The process is repeated for the other two LV electrodes (Mid 3 and Prox 4) to generate paced RV-LV delay values for those LV cathode electrodes as well. The data is forwarded to the programmer for analysis.

Figure 14:
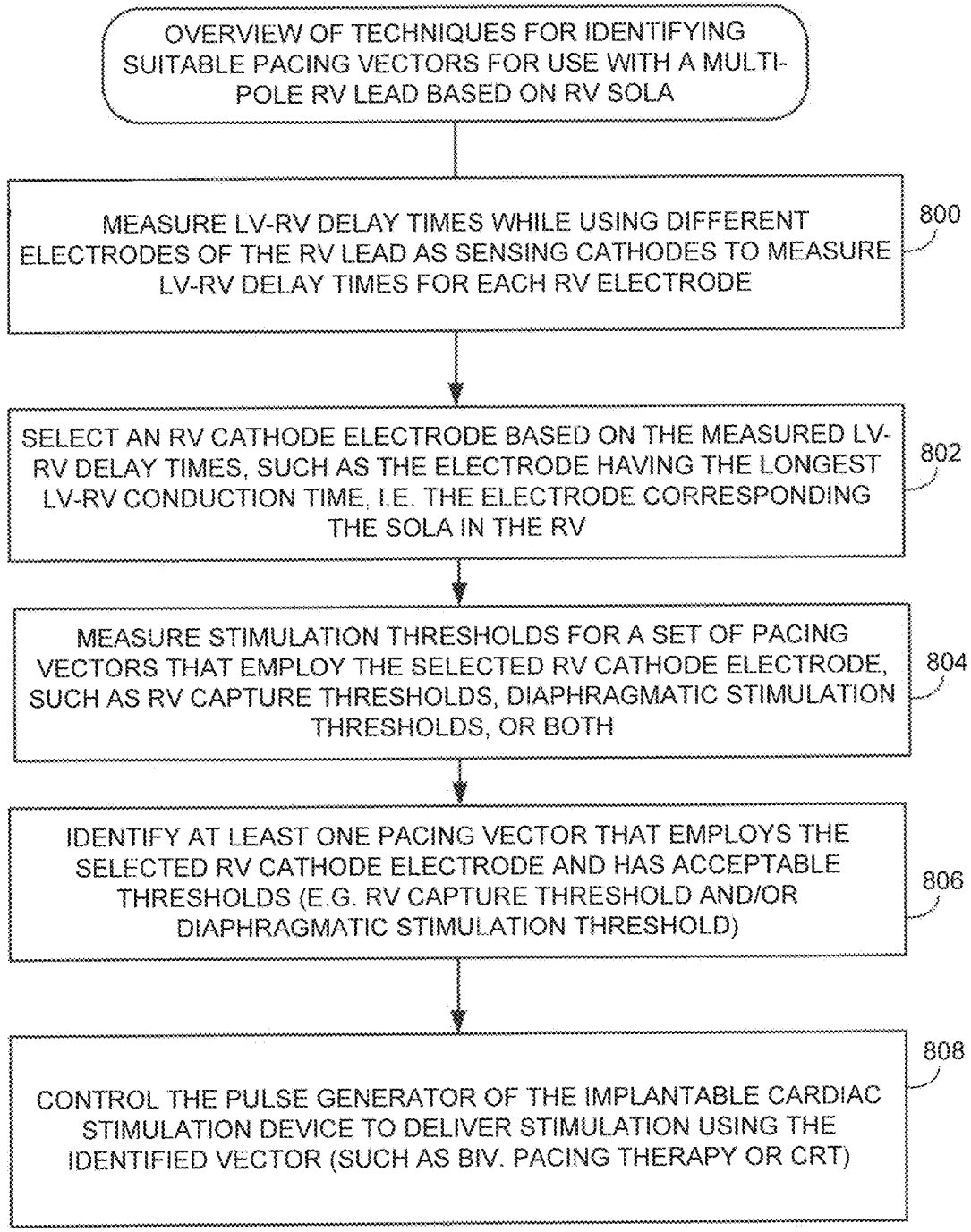
FIG. 14 summarizes an alternative technique for identifying suitable pacing vectors for use with a system having a multi-pole RV lead.

Alternatively, at step 202, the programmer, under the supervision of the clinician, programs the CRT device to measure intrinsic RV-LV delay times for each of the LV electrodes by sensing intrinsic activation in the RV while using the LV electrodes as cathodes to sense LV activation. That is, for a first one of the electrodes of the LV lead (such as Tip 1), the CRT device performs an "RV sense test" wherein intrinsic RV depolarization events are sensed within an RV IEGM (such as a unipolar IEGM sensed RV tip-can) while the LV IEGM is sensed using the particular LV electrode (in this case Tip 1) as a cathode to detect LV activation within an LV IEGM. The time delay between the RV sense observed in the RV IEGM and the LV activation observed in the LV IEGM is the measured RV-LV delay for that particular electrode (Tip 1). As noted above, this value might be negative (if the LV depolarizes before the RV and hence the SOLA is in the RV.) In that case, if the implantable device is equipped with a multi-pole RV lead (FIG. 15), then the procedure can instead be performed using the electrodes of the RV lead to identify the SOLA in the RV (FIG. 14.) The example of FIG. 4 assumes the SOLA is in the LV, as is the case in most heart failure patients. As with the paced RV-LV delays, several intrinsic RV-LV delays may be combined to yield a value for subsequent comparison against other intrinsic RV-LV delays. Then, for a second one of the electrodes of the LV lead (such as Mid 2), the CRT device performs another RV sense test while the LV IEGM is sensed using the selected LV electrode as a cathode to detect LV activation. Intrinsic RV-LV delays for that particular electrode (Mid 2) are measured and combined. The process is repeated for the other two LV electrodes (Mid 3 and Prox 4) to generate intrinsic RV-LV delay values for those LV electrodes as well. The data is forwarded to the programmer for analysis.

Note that RV pace tests and RV sense tests are also discussed in: U.S. Patent Application 2011/0022112 of Min et al., entitled "Systems and Methods for Determining Ventricular Pacing Sites for use with Multi-Pole Leads"; U.S. Patent Application 2011/0022110 of Min et al., entitled "Systems and Methods for Optimizing Ventricular Pacing Delays for use with Multi-Pole Leads"; and U.S. Patent Application 2011/0098772 of Min, entitled "Systems and Methods for Determining Optimal Electrode Pairs for use in Biventricular Pacing using Multi-Pole Ventricular Leads."

At step 204, the programmer receives and analyzes the resulting data from the CRT device and identifies the LV cathode electrode having the longest RV-LV delay time, i.e. the LV electrode corresponding to the SOLA. (Note that the clinician will typically activate either only the RV pace test or only the RV sense test and so the LV cathode electrode having the longest RV-LV delay time is determined by simple examination of the data received from the CRT device. These values are displayed to the clinician for review. At step 206, the programmer, under the supervision of the clinician, programs the CRT device to measure LV capture thresholds and diaphragmatic stimulation thresholds for pacing vectors that employ the selected LV cathode electrode. (Note that the diaphragmatic stimulation thresholds might also be referred to as "phrenic nerve stimulation thresholds.") That is, the programmer sends suitable commands to the CRT device to perform LV capture threshold and diaphragmatic stimulation threshold tests using only the selected vectors. LV capture threshold tests are performed to determine the pulse magnitude above which pacing pulses cause the LV myocardium to depolarize (so as to verify that a particular pacing vector has a capture threshold that is not too high.) The LV capture threshold may differ from one LV location to another and may depend upon the particular vector used to deliver the stimulation. Hence, for a given LV electrode used as a cathode for pacing (such as Tip 1), the capture threshold may differ depending upon the anode that is used (i.e. the RV tip, the RV ring, the RV coil, or one of the other LV electrodes.) Diaphragmatic stimulation threshold tests are performed to determine the pulse magnitude above which pacing pulses cause the diaphragm to contract (so as to verify that a particular pacing vector has a diaphragmatic stimulation threshold that is not too low, since diaphragmatic stimulation is to be avoided.) As with LV capture thresholds, the diaphragmatic stimulation threshold may differ from one LV location to another and may depend upon the particular vector used to deliver stimulation. Hence, for a given LV electrode used as a cathode for pacing, the diaphragmatic stimulation threshold may likewise differ depending upon the anode used.

Accordingly, the CRT device (or the external programmer) performs a separate LV capture threshold test for each vector that uses the LV cathode electrode identified at step 204 to determine if any of the selected vectors has a suitable capture threshold. Consider an example wherein the Distal Tip 1 electrode is found at step 204 to have the longest delay time. For a first vector that uses the Tip 1 as a cathode (such as the RV coil-Tip 1 vector), the CRT device performs an LV capture threshold test to determine the capture threshold for that vector. This may be performed by delivering a series of pacing pulses using that vector with decreasing pulse magnitudes while observing the resulting LV IEGM to determine the lowest pulse magnitude sufficient to evoke capture. Capture threshold tests are described, for example, in U.S. Pat. No. 7,899,536 to Hellman, entitled "Morphology Discrimination for Capture Assessment" See, also, U.S. Pat. No. 7,881,787 to Min, entitled "Capture Detection System and Method CRT Therapy"; U.S. Patent Application 2010/0100148 of Min et al., entitled "Capture Assessment and Optimization of Timing for Cardiac Resynchronization Therapy"; and U.S. Patent Application 2010/0042176 of Snell, entitled "Temporal-Based Cardiac Capture Threshold Detection." The result of the LV capture test will either provide a capture threshold for the vector being tested (above which LV capture is achieved) or will indicate that LV capture cannot be achieved within a programmable range of pacing pulse magnitudes (and hence the vector being tested is unsuitable.)

Then, for a second vector that uses the Tip 1 as the cathode (such as the RV ring-Tip 1 vector), the CRT device (or the external programmer) performs another LV capture threshold test to determine the capture threshold for that vector. The process continues to test each of the programmable vectors that use the selected LV electrode (Tip 1) as a cathode (or for a subset thereof, as specified by the clinician.) In this regard, for biventricular pacing (if specified by the clinician), only RV-LV vectors are typically tested. These may be referred to as "extended" bipolar vectors. For CRT (again as specified by the clinician), interelectrode LV vectors (such as Tip 1-Mid 2 and Tip 1-Mid 3) may additionally or alternatively be tested. These may be referred to as "true" bipolar vectors. Alternatively, the test may be stopped at the first vector that satisfies the capture threshold and diaphragmatic stimulation threshold criteria determined by the user. In some implementations, the results of the various LV capture threshold tests are stored within the CRT device and transmitted to the external programmer for clinician review. Typically, however, the CRT device instead sends IEGM data to the external programmer, which analyzes the data to detect LV capture thresholds under clinician supervision.

Also at step 206, the CRT device performs the diaphragmatic stimulation tests. Accordingly, the CRT device performs a separate diaphragmatic stimulation threshold test for each vector that uses the LV electrode identified at step 204 as a cathode to determine if any of the vectors have a diaphragmatic stimulation threshold that is too low (as may be determined by comparing the measured diaphragmatic thresholds against an acceptable diaphragmatic stimulation threshold value.) Again, consider the example where the Tip 1 electrode is found at step 204 to have the longest delay time. For a first vector that uses the Tip 1 as a cathode (such as the RV coil-Tip 1 vector), the CRT device performs a diaphragmatic stimulation threshold test to determine the diaphragmatic stimulation threshold for that vector. This may be performed by delivering a series of pacing pulses using that vector with increasing pulse magnitudes while sensing diaphragmatic activation using an accelerometer to determine the pulse magnitude above which the diaphragm is inadvertently stimulated. Diaphragmatic stimulation testing is described, for example, in U.S. Pat. No. 7,299,093 to Zhu et al., entitled "Method and Apparatus for Avoidance of Phrenic Nerve Stimulation during Cardiac Pacing", which describes a CRT device in which an accelerometer is used to detect diaphragmatic or other skeletal muscle contraction associated with the output of a pacing pulse. See, also, U.S. Pat. No. 6,772,008 to Zhu. Alternatively, the clinician may simply monitor the patient to determine if diaphragmatic stimulation is occurring. The result of the diaphragmatic test will either provide a diaphragmatic stimulation threshold for the vector being tested (below which diaphragmatic stimulation is avoided) or will indicate that diaphragmatic stimulation cannot be avoided within a programmable range of pacing pulse magnitudes (and hence the vector being tested is unsuitable.)

Then, for a second vector that uses the Tip 1 as a cathode (such as the RV ring-Tip 1 vector), the CRT device performs another diaphragmatic stimulation threshold test to determine the diaphragmatic stimulation threshold for that vector. The process continues to test each of the programmable vectors that use the selected LV electrode (Tip 1) as a cathode (or for a subset thereof, as specified by the clinician.) Alternatively, the test may be stopped at the first vector that satisfies the capture threshold and diaphragmatic stimulation threshold criteria determined by the user. In some implementations, the results of the various diaphragmatic stimulation threshold tests are stored within the CRT device and transmitted to the external programmer for clinician review. Alternatively, however, the CRT device instead sends accelerometer data to the external programmer, which analyzes the data to detect diaphragmatic stimulation, or the clinician merely observes the patient to detect any unwanted diaphragmatic stimulation.

At step 208, the external programmer receives appropriate data from CRT device and analyzes the data to identify candidate vectors, if any, having both a suitable capture threshold and a suitable diaphragmatic threshold. That is, the programmer seeks to identify one or more vectors where pacing pulses can be delivered with sufficient magnitude to reliably trigger LV depolarization while avoiding diaphragmatic stimulation. For some vectors, to achieve LV capture, the pulse magnitude might need to be set so high that diaphragmatic stimulation is also triggered and so such vectors are rejected. For other vectors, LV capture might not be achieved even when the pulse magnitude is set to its highest programmable value and so, again, such vectors are rejected. Assuming that at least one suitable candidate vector is found at step 210, then at step 212 the programmer, under clinician supervision, selects one or more of the candidate vectors for delivering pacing therapy and then programs the CRT device to use the selected vector(s). For example, the programmer may display data for each of the candidate vectors for clinician review (including LV capture thresholds, diaphragmatic thresholds, etc.) to allow the clinician to select one of the vectors for use in delivering pacing therapy to the patient. The clinician's choice of vector (or vectors) is then programmed into the CRT device so that pacing therapy may then be delivered using the programmed vector(s).

Note that if none of the vectors tested at steps 206 and 208 is found to be suitable at step 210 (i.e. no candidate vectors are found), then the programmer, under clinician supervision, programs the CRT device to select the LV electrode having the next longest RV-LV delay time (or some other LV electrode of the clinician's choosing) and the process is repeated to perform LV capture threshold and diaphragmatic stimulation threshold tests for vectors that use the newly selected LV electrode as the cathode. If no vectors are ultimately found that are deemed to be suitable, then the LV lead may need to be repositioned within the patient or other appropriate actions taken.

Figure 4:
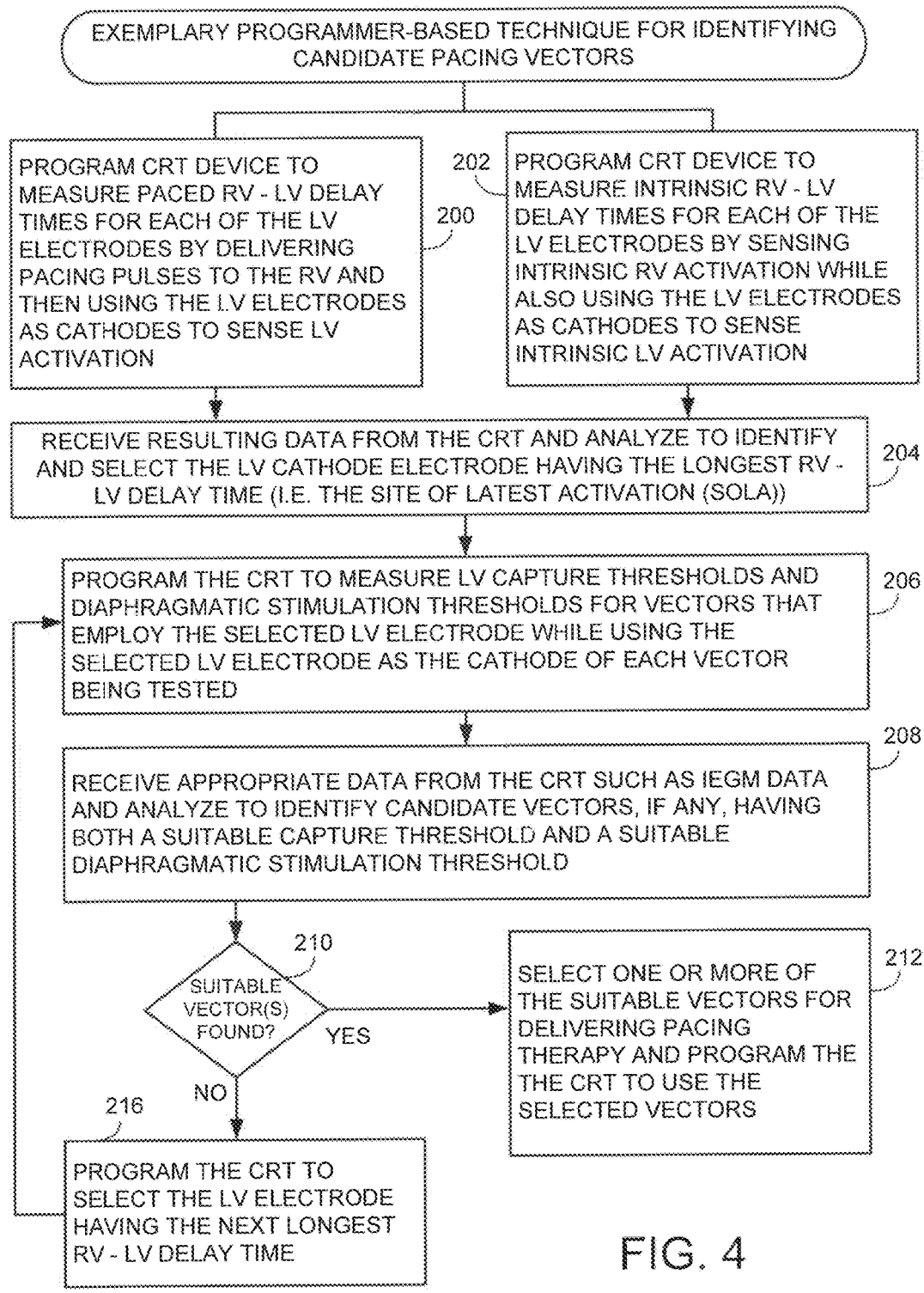
FIG. 4 illustrates a first exemplary implementation of the method of FIG. 3 wherein an external programmer is employed to control the CRT device to perform a series of capture tests under clinician supervision.

FIGS. 5-9 illustrate exemplary display screens that may be displayed by the programmer while the procedure of FIG. 4 is performed. In these examples, some of the intermediate steps of the method are activated by the clinician by pressing various control buttons or tabs on the programmer, but it should be understood that the entire method can be automated so that intermediate clinician input is not necessarily required. Clinician supervision and input is preferred to allow for programming flexibility. When the algorithm is automated in the device, preset criteria for selecting a vector as the one to program to may be input to the device by the clinician such as capture threshold no greater than 1.5V, and diaphragmatic stimulation threshold no lower than 4V.

Figure 5:
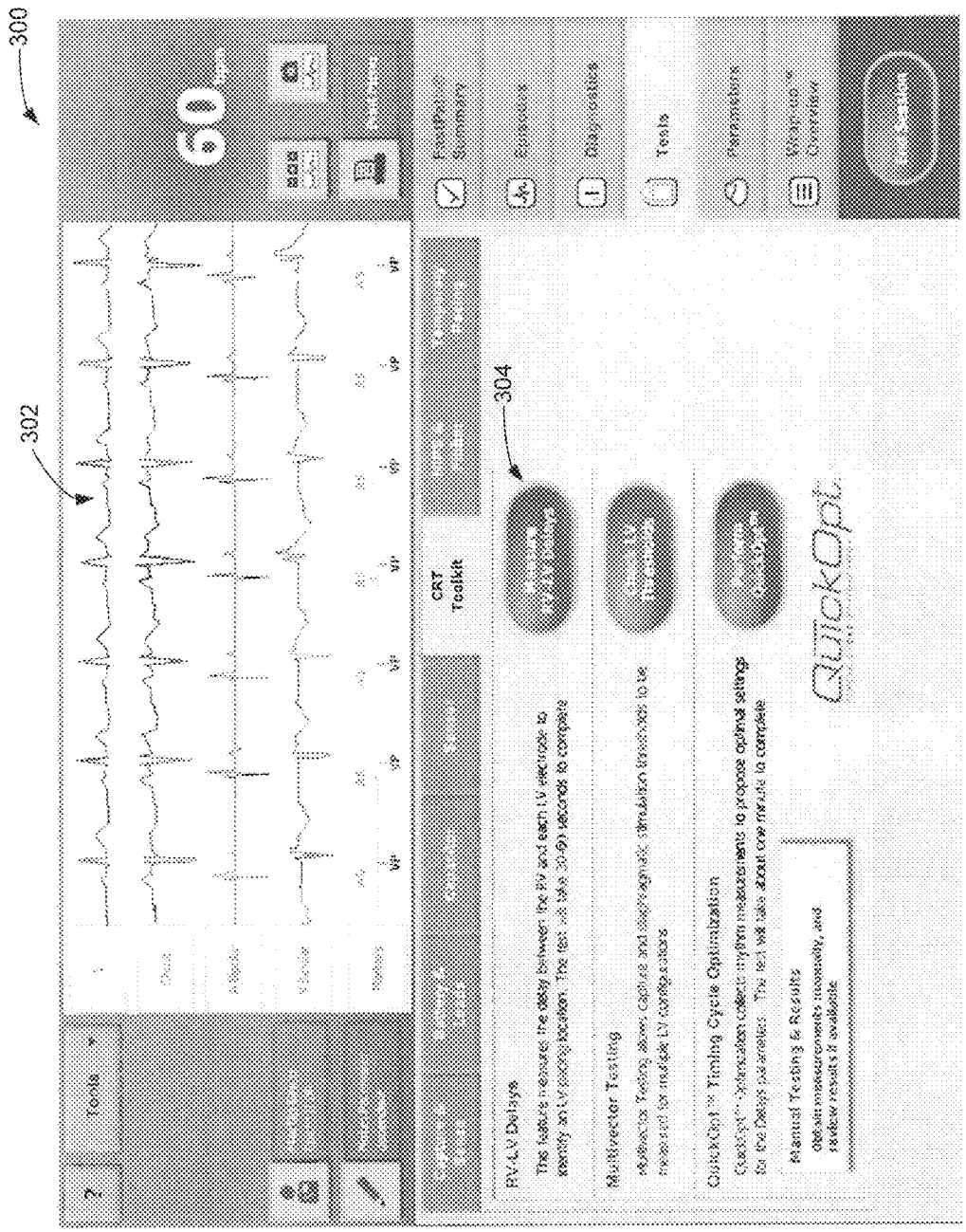
FIG. 5 illustrates an exemplary display screen generated by the programmer during the method of FIG. 4 for entry into an RV-LV delay measurement mode.
Figure 6:
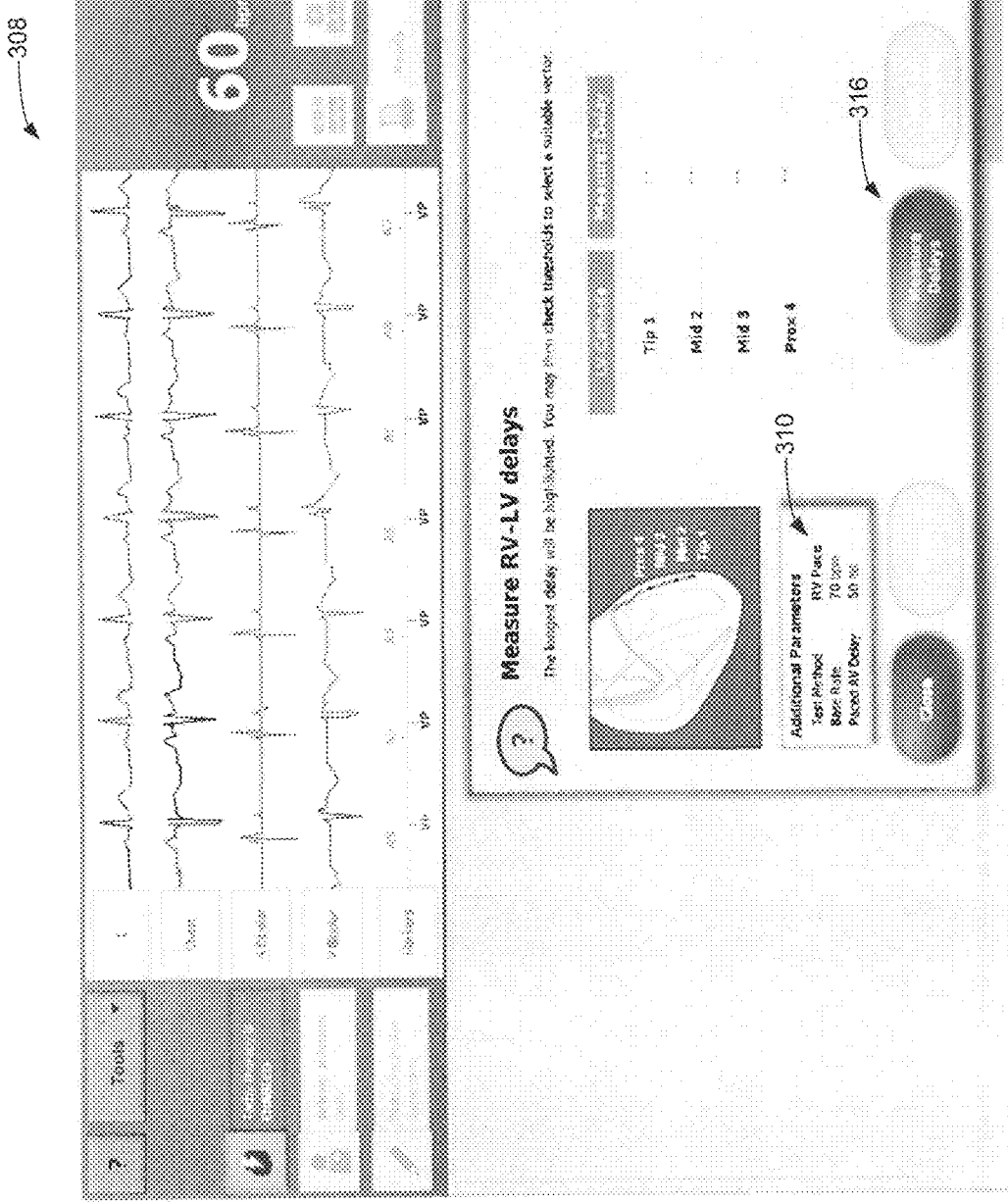
FIG. 6 illustrates an exemplary display screen generated by the programmer during the method of FIG. 4 for controlling the CRT device to measure RV-LV delays for a selected LV cathode electrode.
Figure 7:
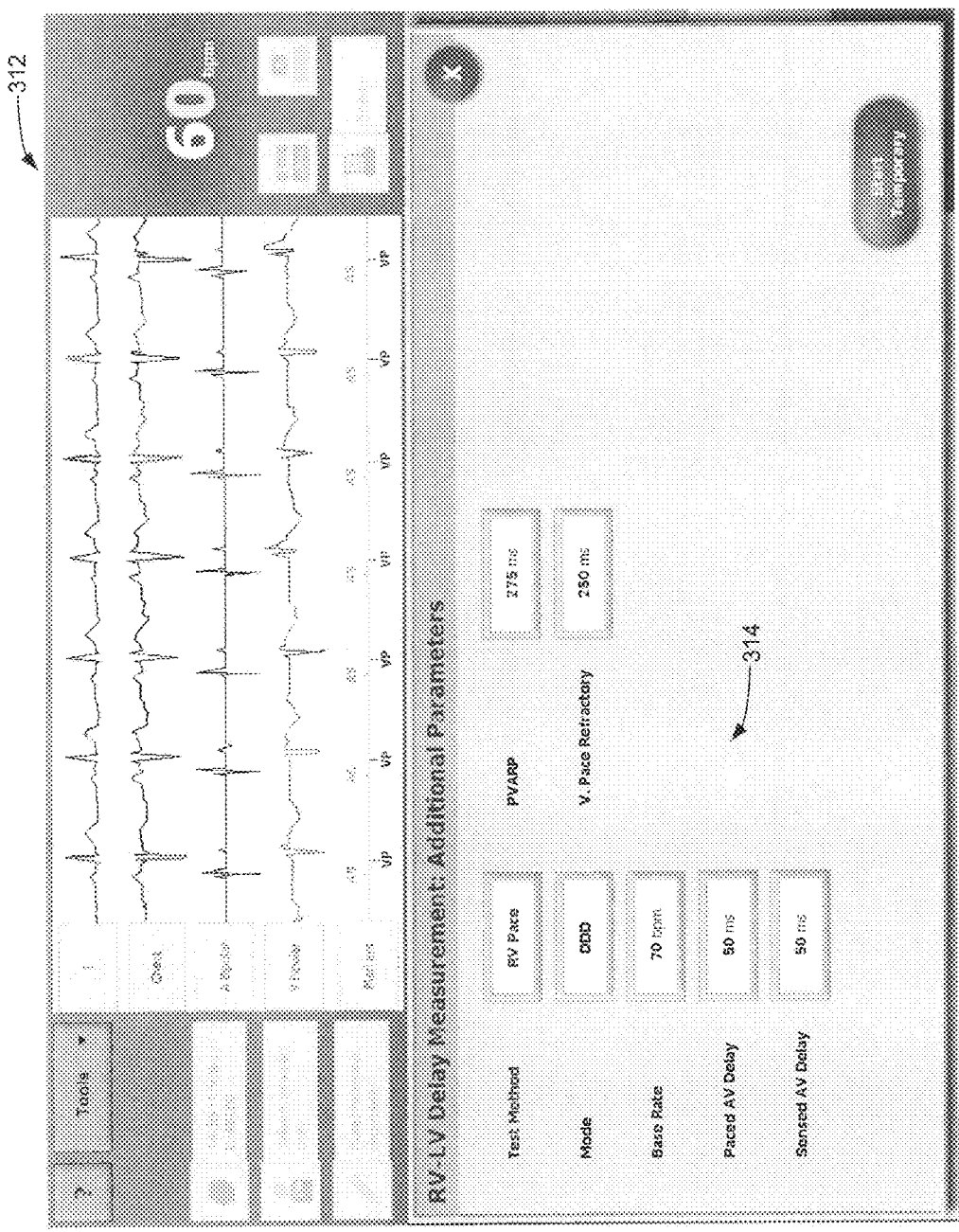
FIG. 7 illustrates an exemplary display screen generated by the programmer during the method of FIG. 4 for allowing further selection of RV-LV delay measurement parameters for use in controlling the CRT device.

Beginning with FIG. 5, a screen 300 is displayed that provides patient data such as IEGUIs 302 and presents various command functions for clinician selection. In particular, the clinician may select function 304 to initiate the aforementioned RV-LV delay tests. In response, the programmer presents screen 308 of FIG. 6, which specifies pertinent test parameters 310 such as the test method (e.g. RV pace with LV sense), the base pacing rate (70 beats per minute (bpm)) and the paced atrioventricular (AV) delay. The clinician may modify these if desired. For example, an RV sense test can instead be activated with LV sense, as described above. FIG. 7 illustrates a display screen 312 that allows the clinician to temporarily adjust various RV-LV delay measurement parameters 314, including mode, base rate, paced AV delay, sensed AV delay, post-ventricular atrial refractory period (PVARP) and the duration of a ventricular paced refractory interval. Returning to FIG. 6, the clinician then selects function 316 to activate the RV-LV delay tests using the currently specified set of parameters. The programmer then transmits the appropriate control signals to the CRT device to cause the CRT device to perform the specified RV-LV delay tests.

Figure 8:
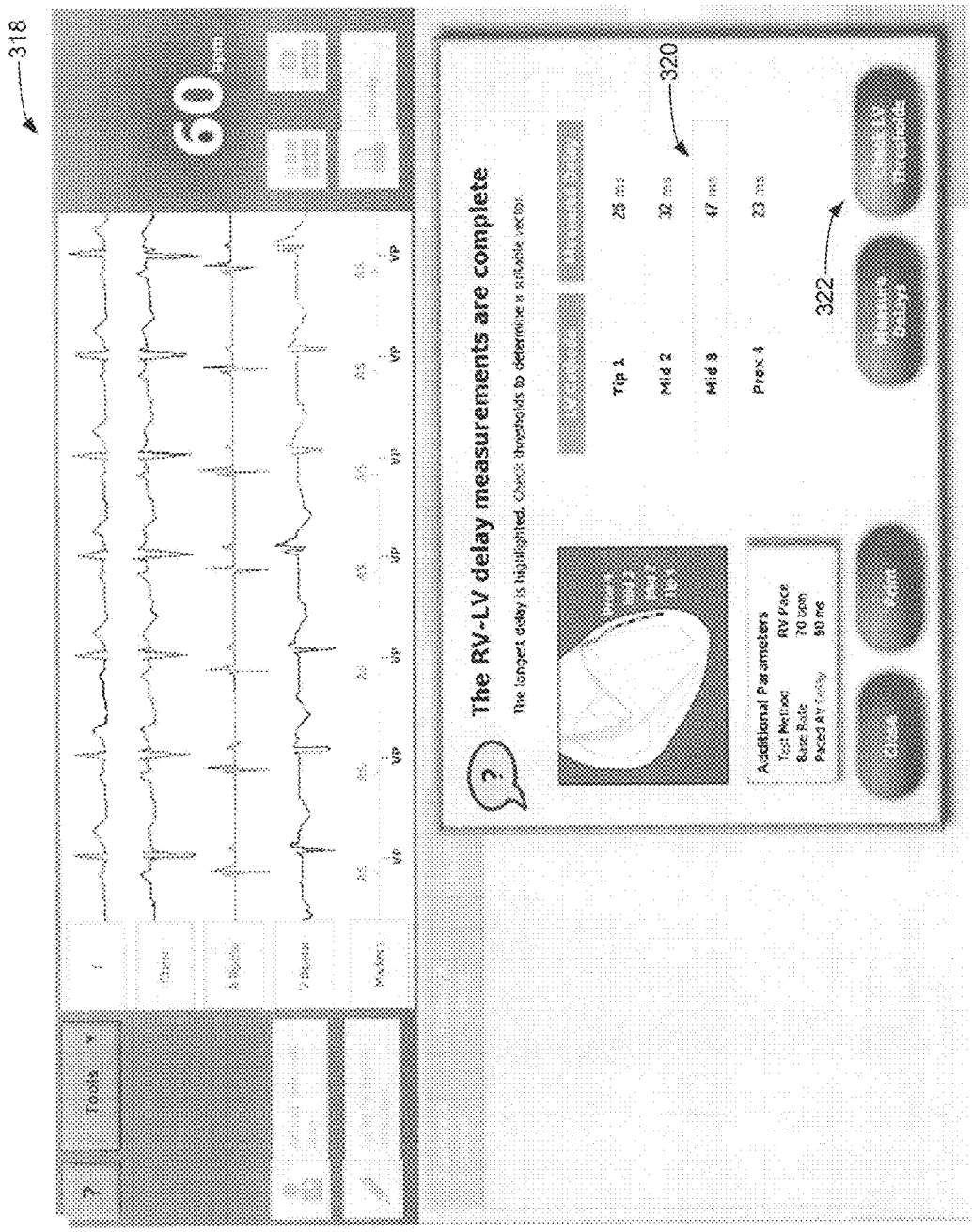
FIG. 8 illustrates an exemplary display screen generated by the programmer during the method of FIG. 4 for displaying measured RV-LV delays and particularly identifying the LV electrode having the SOLA.
Figure 9:
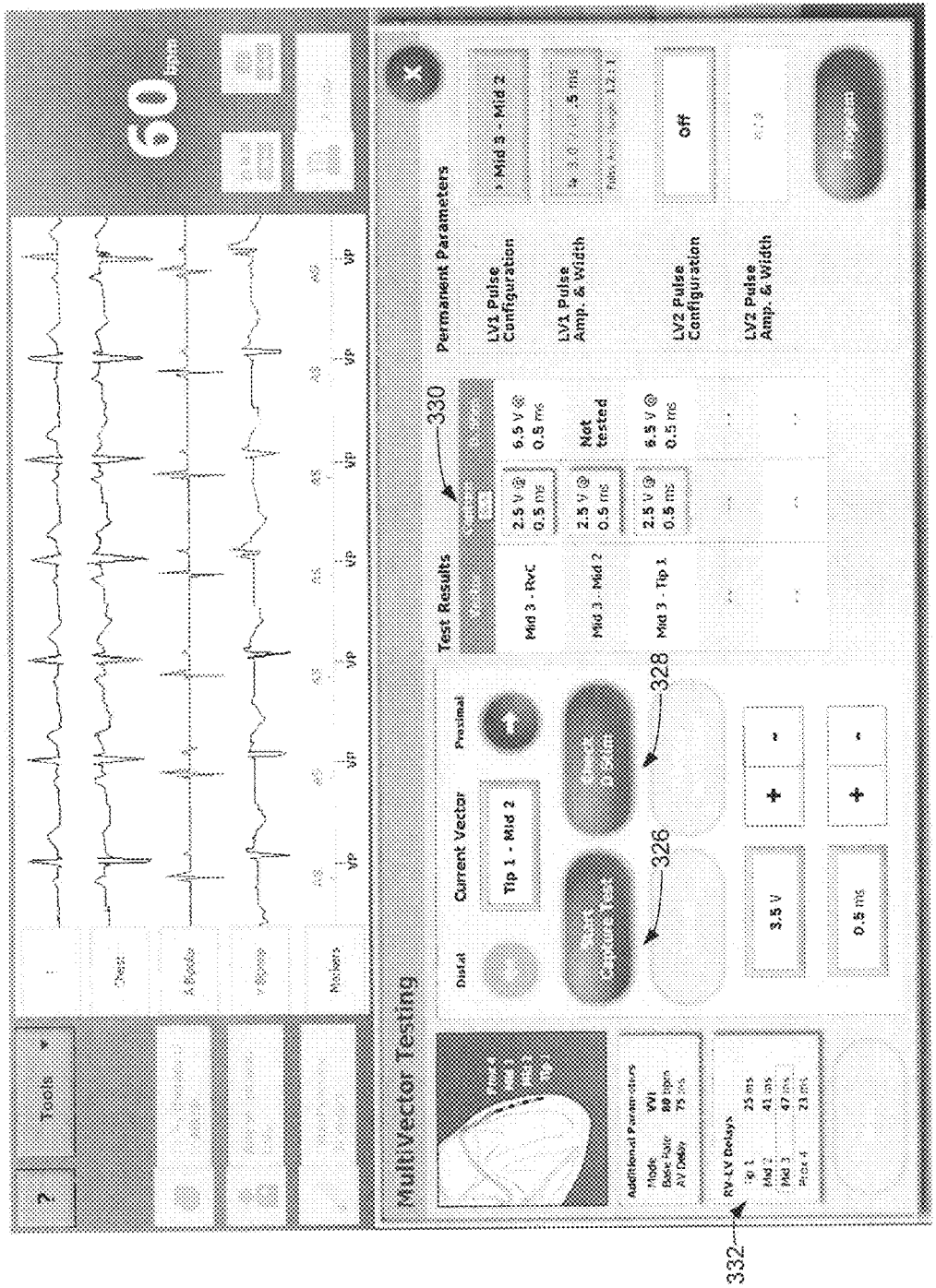
FIG. 9 illustrates an exemplary display screen generated by the programmer during the method of FIG. 4 for controlling the CRT device to perform capture tests and diaphragmatic stimulation tests.

After the CRT device has performed the RV-LV delay tests, the resulting data is transmitted to the programmer and displayed via screen 318 of FIG. 8 so that the clinician can easily identify the LV electrode having the longest RV-LV delay (i.e. the LV electrode representing the SOLA.) In this example, it is the Mid 3 electrode with a delay of 47 ms, as indicated by highlighted block 320. The clinician then may select function 322 to display a capture threshold test screen for vectors using Mid 3 as a cathode. In response, the programmer displays the MultiVector Testing screen 324 of FIG. 9, which allows the clinician to activate the LV capture test function 326 or the diaphragmatic test function 328. Again, appropriate control signals are then sent to the CRT device causing the CRT device to perform the capture tests and the appropriate resulting data such as IEGM data is received from the CRT device. In this example, the results of the capture tests for the Mid 3 electrode and three of the vectors using that electrode as a cathode (specifically Mid 3-RV coil, Mid 3-Mid 2 and Mid 3-Tip 1 are displayed in test result block 330, as shown. Note that the clinician still has the flexibility to test any other vectors if desired. In addition, RV-LV delay measurement results are again displayed as shown by way of block 332. If none of the vectors associated with Mid 3 is deemed to have acceptable capture and/or diaphragmatic stimulation thresholds, further testing of vectors associated with the LV electrode having the second longest delay can be performed. In the example in FIG. 9, the next set of vectors to be tested would then be vectors associated with Mid 2. Thereafter, the clinician can easily select the final appropriate LV vector for programming with no diaphragmatic stimulation and an appropriate LV capture threshold. Using this procedure or workflow, the clinician thereby is provided with guidance in testing and programming LV lead configurations to reduce lead positioning and vector selection testing time significantly while providing flexibility to the clinician.

Thus, FIGS. 4-9 illustrate a programmer-based implementation wherein the procedure is performed under clinician supervision. It expected that the procedure would be performed once or twice per year to reprogram the device, if needed. By reducing the number of tests that the clinician typically needs to perform, the workflow of the clinician is thereby simplified to make the overall vector identification procedure more efficient. In particular, the interactions of various different tests (i.e. LV capture tests and diaphragmatic stimulation threshold tests) are simplified and streamlined.

Exemplary LV SOLA Techniques Employed by a CRT Device

Figure 10:
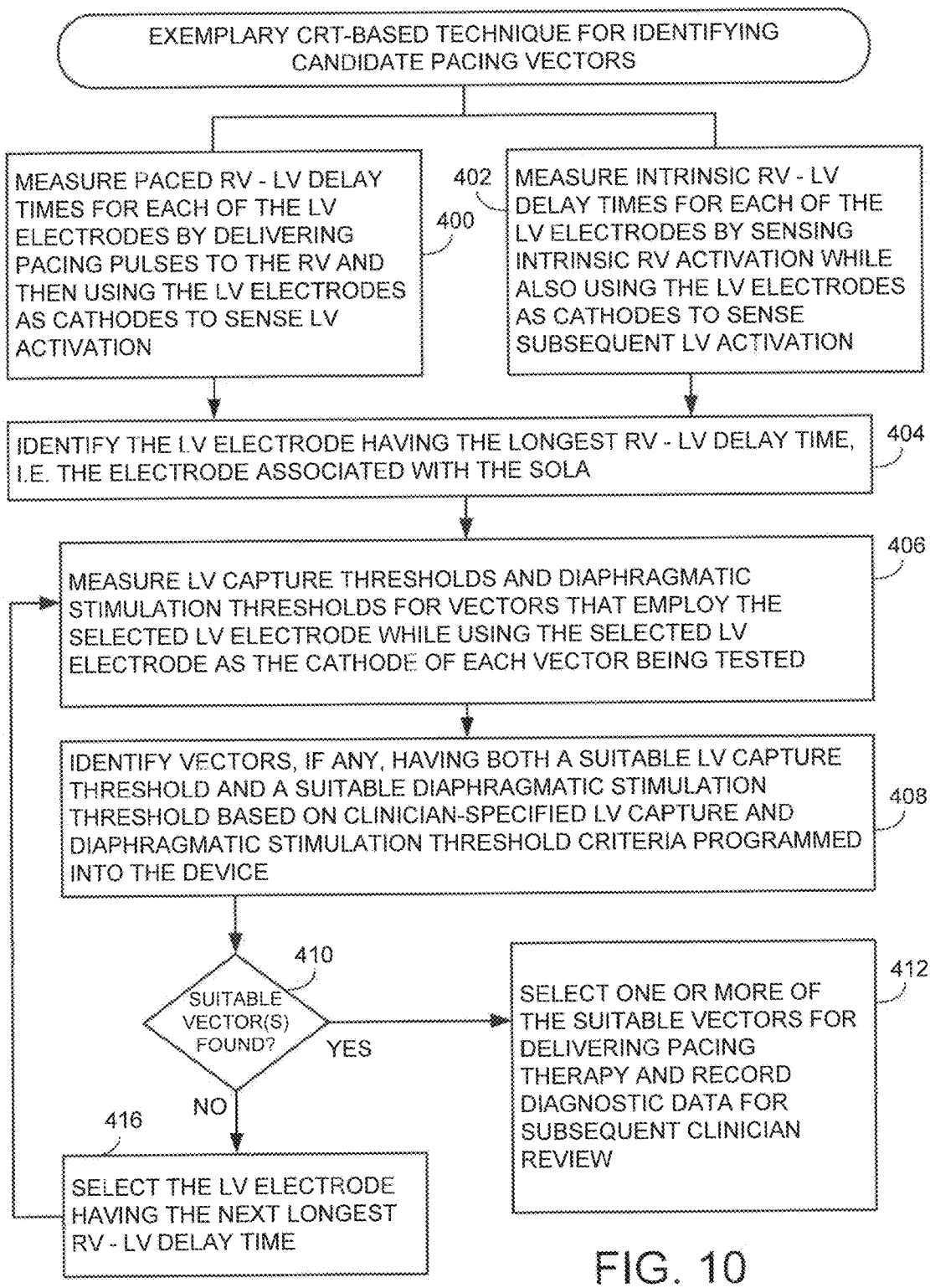
FIG. 10 illustrates a second exemplary implementation of the method of FIG. 3 wherein the CRT device performs the various steps of the method.

FIG. 10 illustrates an alternative implementation where the CRT device is equipped to automatically perform the pacing vector selection techniques, as might be warranted in response to a persistent LV LOC due to lead migration, particularly if clinician-supervised reprogramming is not readily available. Many of the steps are similar to those of FIG. 4 and hence will not be described again in detail. Briefly, beginning at step 400 of FIG. 10, the CRT device measures paced RV-LV delay times for each of the LV electrodes by delivering pacing pulses to the RV while using the LV electrodes as cathodes to sense LV activation, i.e. the CRT device performs RV pace tests for each of LV electrodes. Alternatively, depending upon device programming, the CRT device at step 402 measures intrinsic RV-LV delay times for each of the LV electrodes, i.e. the CRT device performs RV sense tests while using the LV electrodes as cathodes.

At step 404, the CRT device and identifies the LV electrode having the longest RV-LV delay time based on the paced RV-LV delays or intrinsic RV-LV delays. At step 406, the CRT device measures capture thresholds and diaphragmatic thresholds for vectors that employ the selected LV electrode (while using the selected LV electrode as a cathode.) At step 408, the CRT device analyzes the capture threshold and diaphragmatic stimulation threshold data to identify vectors, if any, having both a suitable capture threshold and a suitable diaphragmatic threshold. This may be performed based on clinician-specified LV capture and diaphragmatic stimulation threshold criteria programmed into the device. Assuming that at least one suitable vector is found at step 410, then at step 412 the CRT device selects one or more of the suitable vectors for delivering pacing therapy (by, for example, selecting the candidate vector having the lowest LV capture threshold) and records diagnostic data for subsequent clinician review. (Typically, the test is stopped after finding the first suitable vector.) If none of the vectors tested at steps 406 and 408 is found to be suitable, then the CRT device selects the LV electrode having the next longest RV-LV delay time and the process is repeated to perform LV capture threshold and diaphragmatic stimulation threshold tests for vectors that use the newly selected LV electrode as a cathode. If no vectors are found that are deemed to be suitable, pacing is disabled. In any case, suitable warning signals are generated to alert the patient or caregiver that the pacing vector needed to be changed so that the patient can then consult a clinician as soon as possible who will review the diagnostic data and modify CRT device programming, if warranted.

Note that the various techniques described herein can be used, where appropriate, in conjunction with other programming and/or optimization techniques. See, for example, techniques for determining preferred or optimal interventricular (VV) delays between the LV and RV electrodes using interventricular delay-based quick optimization techniques (QuickOpt™) QuickOpt™ techniques are discussed in U.S. Pat. No. 7,248,925 to Bruhns et al., entitled "System and Method for Determining Optimal Atrioventricular Delay based on Intrinsic Conduction Delays" and in at least some of the following patent documents: U.S. Patent Published Application No. 2005/0125041, entitled "Methods for Ventricular Pacing"; U.S. patent application Ser. No. 10/974,123, filed Oct. 26, 2004; U.S. Pat. No. 7,590,446; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007. See, also, U.S. Published Patent Application No. 2010/0145405, entitled "Systems and Methods for Controlling Ventricular Pacing in Patients with Long Intra-Atrial Conduction Delays", U.S. Published Patent Application No. 2009/0299423, entitled "Systems and Methods for determining Intra-Atrial Conduction Delays using Multi-Pole Left Ventricular Pacing/Sensing Leads", and U.S. Published Patent Application No. 2011/0022106, entitled "Systems and Methods for Optimizing Ventricular Pacing Delays During Atrial Fibrillation."

See, also, the following patents and patent applications that set forth various systems and methods for determining and/or adjusting AV/VV pacing delays so as to help maintain the pacing delays at preferred or optimal values: U.S. Pat. No. 7,590,446; U.S. Published Patent Application 2009/0299423; U.S. patent application Ser. No. 11/952,743 filed Dec. 7, 2007; U.S. Published Patent Application No. 2010/0145405; U.S. Published Patent Application No. 2011/0022110; U.S. Published Patent Application No. 2011/0022112; and U.S. Patent Application 2011/0098772 of Min et al., entitled "Systems and Methods for Determining Optimal Electrode Pairs for use in Biventricular Pacing using Multi-Pole Ventricular Leads."

What have been described are various techniques for expediting pacing vector selection for use with biventricular pacing or CRT to determine optimal pacing vector(s). It should be understood that these optimal vectors are not necessarily truly optimal in any particular quantifiable sense. As can be appreciated, what constitutes a truly "optimal" vector depends on the criteria used for judging the resulting performance, which can be subjective in the minds of some clinicians. Accordingly, the pacing vectors identified herein are at least "preferred" pacing vectors. Clinicians may choose to adjust or alter the selection via device programming for particular patients, at their discretion. Note also that, in the examples described herein, the multi-pole ventricular lead is an LV lead but it should be understood that aspects of the invention are applicable to multi-pole RV leads. Indeed, at least some of the techniques described herein are generally applicable to implementations wherein both the LV and RV have multi-pole leads. At least some of the techniques might be applicable to multi-pole atrial leads, implanted on or in either the RA or the LA/CS.

Although primarily described with respect to examples wherein the CRT device has CRT capability, other implantable medical devices may be equipped to exploit the techniques described herein. For the sake of completeness, an exemplary CRT device will now be described, which includes components for performing the functions and steps already described, as well as components for controlling CRT.

Exemplary CRT Device

Figure 11:
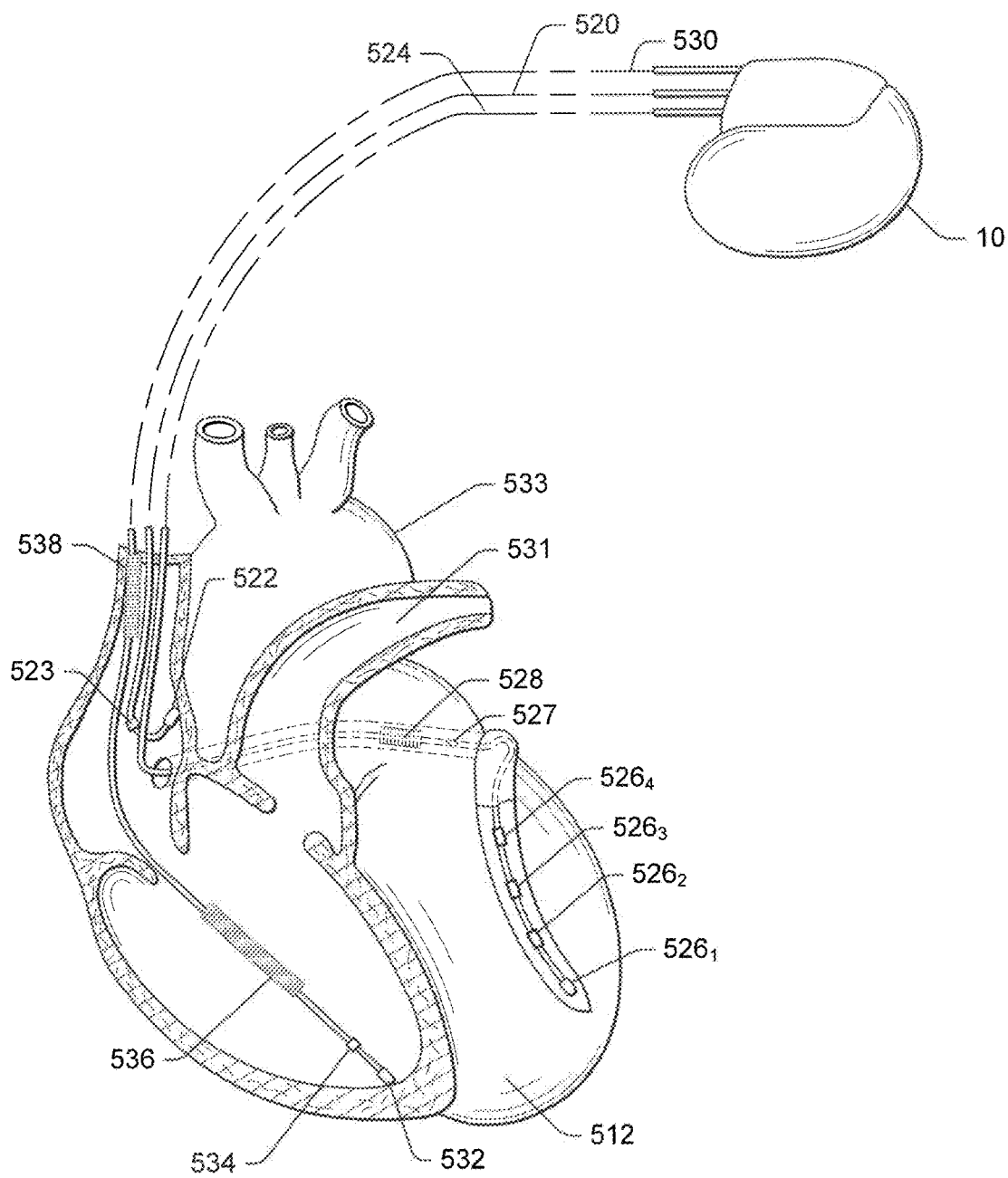
FIG. 11 is a simplified, partly cutaway view, illustrating the device of FIG. 1 along with a set of leads implanted into the heart of the patient.
Figure 12:
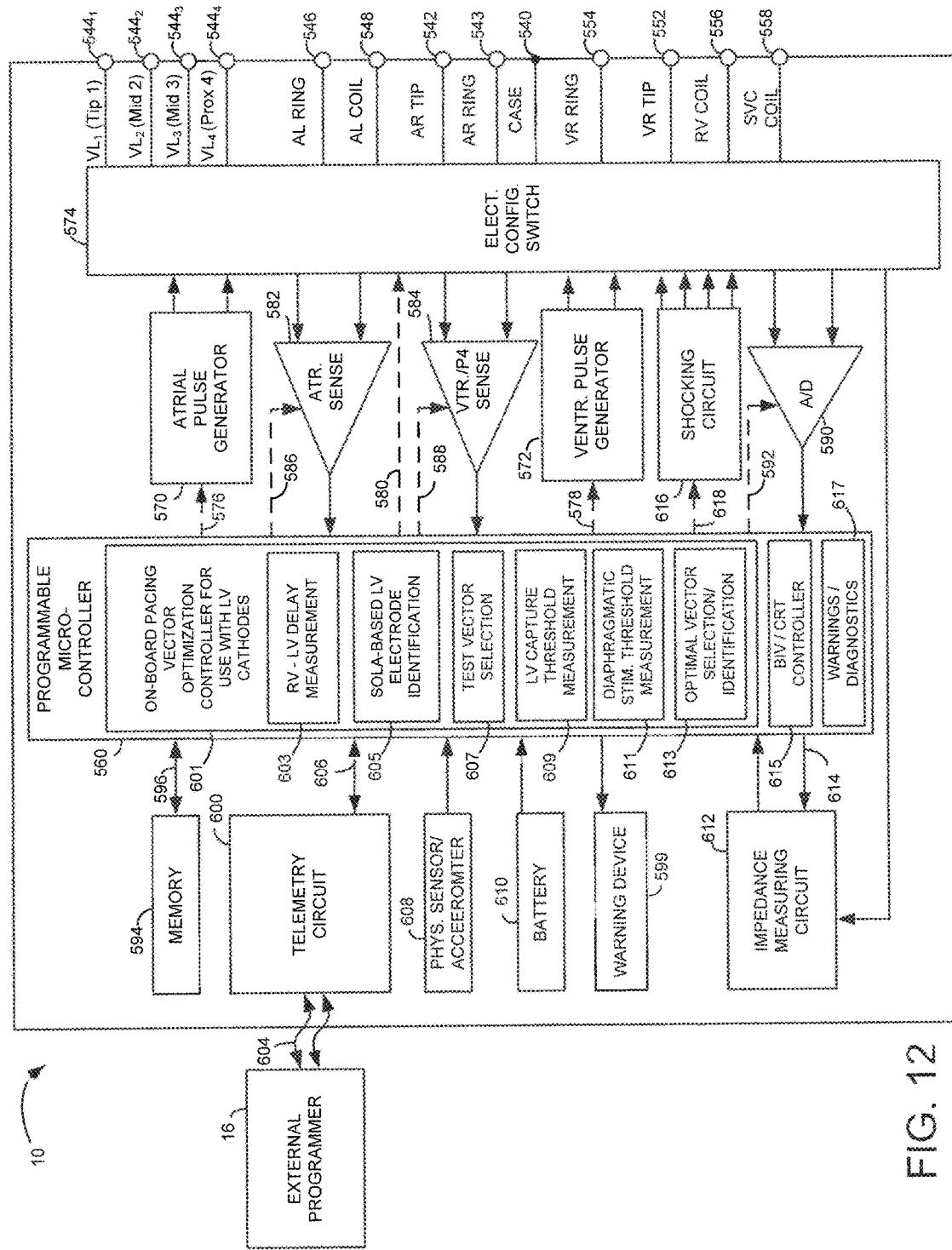
FIG. 12 is a functional block diagram of the CRT device of FIG. 11, illustrating basic circuit elements that provide cardioversion, defibrillation and/or pacing stimulation in the heart an particularly illustrating on-board components for use with the vector selection techniques of FIGS. 3-10.

With reference to FIGS. 11 and 12, a description of an exemplary CRT device will now be provided. FIG. 11 provides a simplified block diagram of the CRT device, which is a dual-chamber stimulation device capable of treating both fast and slow arrhythmias with stimulation therapy, including cardioversion, defibrillation, and pacing stimulation, and also capable of setting pacing vectors as discussed above. To provide right atrial chamber pacing stimulation and sensing, CRT device 10 is shown in electrical communication with a heart 512 by way of a right atrial lead 520 having an atrial tip electrode 522 and an atrial ring electrode 523 implanted in the atrial appendage. CRT device 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode

538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRT device 10 is coupled to a multi-pole LV lead 524 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 524 is designed to receive atrial and ventricular cardiac signals and to deliver left ventricular pacing therapy using a set of four left ventricular electrodes $526_1$ (Tip 1), $526_2$ (Mid 2), $526_3$ (Mid 3), and $526_4$ (Prox 4), (thereby providing a quadripolar lead), left atrial pacing therapy using at least a left atrial ring electrode 527, and shocking therapy using at least a left atrial coil electrode 528. The $526_1$ LV electrode may also be referred to as a "tip" or "distal" LV electrode. The $526_4$ LV electrode may also be referred to as a "proximal" LV electrode. In other examples, more or fewer LV electrodes are provided. Although only three leads are shown in FIG. 11, it should also be understood that additional leads (with one or more pacing, sensing and/or shocking electrodes) might be used and/or additional electrodes might be provided on the leads already shown, such as additional electrodes on the RV lead. It is also noted that, on present commercially-available hardware, there is often no separate electrode 527. That is, the Prox 4 electrode $526_4$ and the "left atrial ring electrode" 527 are the same. Both electrodes are shown for the sake of completeness and generality.

A simplified block diagram of internal components of CRT device 10 is shown in FIG. 12. While a particular CRT device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 540 for CRT device 10, shown schematically in FIG. 12, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, $544_1$-$544_4$, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes a left ventricular tip terminal ($VL_1$ TIP) $544_1$ and additional LV electrode terminals $544_2$,$544_4$ for the other LV electrodes of the LV lead.

The connector also includes a left atrial ring terminal ($A_L$ RING) 546 and a left atrial shocking terminal ($A_L$ COIL) 548, which are adapted for connection to the left atrial ring electrode 527 and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($V_R$ COIL) 556, and an SVC shocking terminal (SVC COIL) 558, which are adapted for connection to the right ventricular tip electrode 532, right ventricular ring electrode 534, the $V_R$ coil electrode 536, and the SVC coil electrode 538, respectively.

At the core of CRT device 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 12, an atrial pulse generator 570 and a ventricular pulse generator 572 generate pacing stimulation pulses for delivery by the right atrial lead 520, the right ventricular lead 530, and/or the LV lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art. The switch also switches among the various LV electrodes and the various pacing vectors that use the LV electrodes as cathodes.

Atrial sensing circuits 582 and ventricular sensing circuits 584 may also be selectively coupled to the right atrial lead 520, LV lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables CRT device 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, CRT device 10 utilizes the atrial and ventricular sensing circuits, 582 and 584, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the LV lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of CRT device 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRT device 10 may be non-invasively programmed into the memory 594 through a telemetry circuit 600 in telemetric communication with the external device 16, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of CRT device 10 (as contained in the microcontroller 560 or memory 594) to be sent to the external device 16 through an established communication link 604. CRT device 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV delay, VV delay, etc.) at which the atrial and ventricular pulse generators, 570 and 572, generate stimulation pulses. While shown as being included within CRT device 10, it is to be understood that the physiologic sensor 608 may also be external to CRT device 10, yet still be implanted within or carried by the patient. A common type of rate responsive sensor is an activity sensor incorporating an accelerometer or a piezoelectric crystal, which is mounted within the housing 540 of CRT device 10. Other types of physiologic sensors are also known, for example, sensors that sense the oxygen content of blood, respiration rate and/or minute ventilation, pH of blood, ventricular gradient, etc. The accelerometer may be positioned and configured to detect signals representative of diaphragmatic stimulation.

The CRT device additionally includes a battery 610, which provides operating power to all of the circuits shown in FIG. 12. The battery 610 may vary depending on the capabilities of CRT device 10. If the system only provides low voltage therapy, a lithium iodine or lithium copper fluoride cell typically may be utilized. For CRT device 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, appropriate batteries are employed.

As further shown in FIG. 12, CRT device 10 has an impedance measuring circuit 612, which is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, and detecting cardiogenic impedance, etc. The impedance measuring circuit 612 is advantageously coupled to the switch 674 so that any desired electrode may be used.

In the case where CRT device 10 is intended to operate as an ICD device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 40 joules), delivered asynchronously (since R-waves may be too disorganized), and pertaining exclusively to the treatment of fibrillation. Accordingly, the microcontroller 560 is capable of controlling synchronous or asynchronous delivery of shocking pulses.

An internal warning device 599 may be provided for generating perceptible warning signals to the patient via vibration, voltage or other methods.

Insofar as expedited vector selection is concerned, the microcontroller includes an on-board pacing vector optimization controller 601 for use in controlling pacing vector selection either in conjunction with an external programmer (FIGS. 3-9) under clinician supervision or independently (FIG. 10), if so equipped. In this example, the controller includes components for optimizing or expediting the identification of suitable pacing vectors by exploiting LV electrodes as cathodes. Controller 601 includes an RV-LV delay measurement system 603 operative to measure RV-LV delay times for a set of RV-LV vectors while using electrodes of the LV lead as cathodes. The controller also includes a SOLA-based LV electrode identification system 605 operative to identify the LV electrode having the longest RV-LV delay time, i.e. the LV electrode corresponding to the SOLA. A test vector selection system 607 is operative to identify a set of vectors for testing that use the LV electrode identified by system 605 as the cathode of the vector. An LV capture threshold measurement system 609 is operative to measure capture thresholds for vectors that employ the selected LV electrode. A diaphragmatic stimulation threshold measurement system 611 is operative to measure diaphragmatic thresholds for vectors that employ the selected LV electrode. An optimal vector identification system 613 is operative to identify one or more vectors that employ the selected LV electrode and have an acceptable capture thresholds and diaphragmatic thresholds, i.e. vectors that are deemed to be preferred, optimal or otherwise suitable for delivering pacing therapy. A biventricular/CRT controller 615 is operative to control biventricular pacing therapy, CRT or other forms of therapy using one or more of the identified vectors. A warnings/diagnostics controller 617 is operative to control the storage of diagnostics data for transmission to the external programmer 16 and to control the generation of any warning signals, if warranted. Diagnostic data can be stored within memory 594. Warning signals may be generated via warning device 599.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, a detailed description of an exemplary programmer will now be provided.

Exemplary External Programmer

Figure 13:
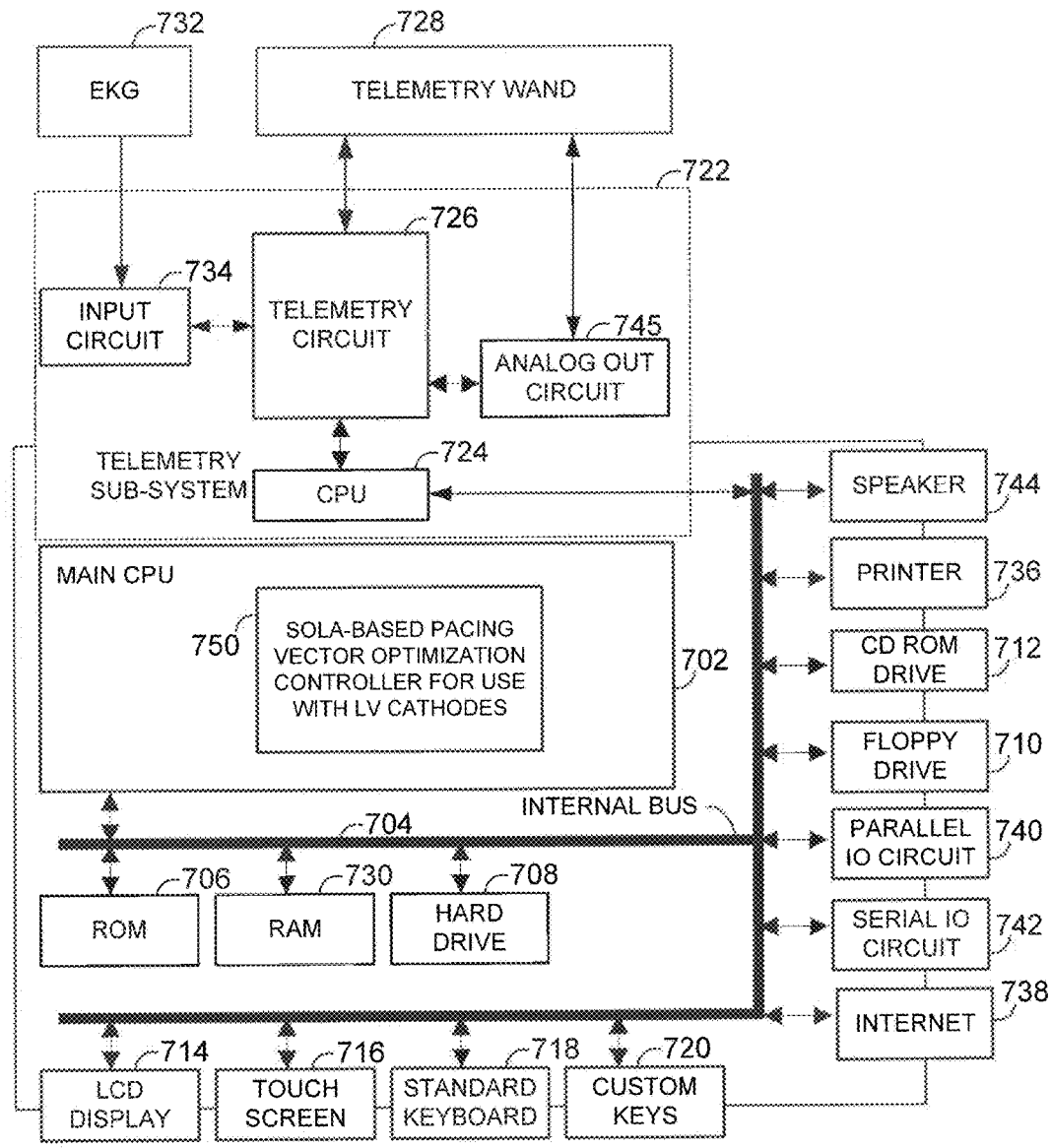
FIG. 13 is a functional block diagram illustrating components of the external programmer of FIG. 1, particularly illustrating programmer-based components for controlling the vector selection techniques of FIGS. 3-10.

FIG. 13 illustrates pertinent components of an external programmer 16 for use in programming the CRT device of FIGS. 11 and 12 and for performing the above-described vector selection and optimization techniques. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 16 may also be capable of processing and analyzing data received from the implanted device and from the EKG leads to, for example, render preliminary diagnosis as to medical conditions of the patient or to the operations of the implanted device.

Now, considering the components of programmer 16, operations of the programmer are controlled by a CPU 702, which may be a generally programmable microprocessor or microcontroller or may be a dedicated processing device such as an application specific integrated circuit (ASIC) or the like. Software instructions to be performed by the CPU are accessed via an internal bus 704 from a read only memory (ROM) 706 and random access memory 730. Additional software may be accessed from a hard drive 708, floppy drive 710, and CD ROM drive 712, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 714 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 716 overlaid on the LCD display or through a standard keyboard 718 supplemented by additional custom keys 720, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 16 to retrieve data stored within any implanted devices and to also retrieve EKG data from EKG leads, if any, coupled to the patient. To this end, CPU 702 transmits appropriate signals to a telemetry subsystem 722, which provides components for directly interfacing with the implanted devices, and the EKG leads. Telemetry subsystem 722 includes its own separate CPU 724 for coordinating the operations of the telemetry subsystem. Main CPU 702 of programmer communicates with telemetry subsystem CPU 724 via internal bus 704. Telemetry subsystem additionally includes a telemetry circuit 726 connected to telemetry wand 728, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an input circuit 734 for receiving surface EKG signals from a surface EKG system 732. In other implementations, the EKG circuit is not regarded as a portion of the telemetry subsystem but is regarded as a separate component.

Insofar as data retrieval from an implantable device is concerned, see: U.S. Pat. No. 5,833,623 to Mann et al., entitled "System and Method for Facilitating Rapid Retrieval and Evaluation of Diagnostic Data Stored by an Implantable Medical Device."

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the CRT device also includes the data stored within the recalibration database of the CRT device (assuming the CRT device is equipped to store that data.) Data retrieved from the implanted devices is stored by external programmer 16 either within a random access memory (RAM) 730, hard drive 708 or within a floppy diskette placed within floppy drive 710. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 16, the implanted devices may be further controlled to transmit additional data in real time as it is detected by the implanted devices, such as additional IEGM data, lead impedance data, and the like. Additionally, or in the alternative, telemetry subsystem 722 receives EKG signals from EKG leads 732 via an EKG processing circuit 734. As with data retrieved from the implanted device itself, signals received from the EKG leads are stored within one or more of the storage devices of the external programmer. Typically, EKG leads output analog electrical signals representative of the EKG. Accordingly, EKG circuit 734 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 702, the programming commands are converted to specific programmable parameters for transmission to the implanted devices via telemetry wand 728 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 736.

Programmer/monitor 16 also includes an internet connection 738 to permit direct transmission of data to other programmers via the public switched telephone network (PSTN) or other interconnection line, such as a T1 line, fiber optic cable, Wi-Fi, cellular network, etc. Depending upon the implementation, the modem may be connected directly to internal bus 704 may be connected to the internal bus via either a parallel port 740 or a serial port 742. Other peripheral devices may be connected to the external programmer via parallel port 740 or a serial port 742 as well. Although one of each is shown, a plurality of input output (IO) ports might be provided. A speaker 744 is included for providing audible tones to the user, such as a warning beep in the event improper input is provided by the physician. Telemetry subsystem 722 additionally includes an analog output circuit 745 for controlling the transmission of analog output signals, such as IEGM signals output to an EKG machine or chart recorder.

Insofar as vector selection and optimization pacing is concerned, main CPU 702 includes a SOLA-based pacing vector optimization controller 750 for use controlling pacing vector selection in conjunction with a CRT device (FIGS. 3-9) under clinician supervision. The controller includes components (corresponding to those of controller 601 of FIG. 12) for optimizing or expediting the identification of pacing vectors by exploiting LV electrodes as cathodes. Depending upon the implementation, the various components of the CPU may be implemented as separate software modules or the modules may be combined to permit a single module to perform multiple functions. In addition, although shown as being components of the CPU, some or all of these components may be implemented separately, using ASICs or the like.

The descriptions provided herein with respect to FIG. 13 are intended merely to provide an overview of the operation of programmer and are not intended to describe in detail every feature of the hardware and software of the programmer nor to provide an exhaustive list of the functions performed by the programmer.

Exemplary RV SOLA Techniques

FIG. 14 broadly summarizes techniques for use by a device equipped with a multi-pole RV lead for identifying suitable pacing vectors, especially for use with patients with RBBB where the SOLA is in the RV. Beginning at step 800, LV-RV delay times are measured while using the different electrodes of the RV lead as cathodes for sensing to measure LV-RV delay times for each RV electrode. For example, a set of time delay tests may be performed based on either paced or sensed events in the LV while sensing the RV IEGM to detect resulting interventricular delay times. At step 802, an RV electrode is selected based on the measured LV-RV delays times, preferably the RV electrode having the longest LV-RV delay time (i.e. the electrode having the RV SOLA.) At step 804, stimulation thresholds are measured for a set of pacing vectors that employ the selected RV cathode electrode. For example, a set of RV capture threshold tests and diaphragmatic stimulation tests may be performed, in which pacing pulses of different magnitudes are delivered for each of the set of vectors while the RV IEGM is analyzed to detect RV evoked responses (i.e. RV capture) and while accelerometer signals are analyzed to detect diaphragmatic stimulation. At step 806, one or more vectors are identified that employ the selected RV electrode and have acceptable thresholds. If none of the vectors tested at step 804 have acceptable thresholds, a different RV cathode electrode can be selected at step 802 and the process repeated until a suitable vector is found. At step 808, the pulse generator of the CRT device is controlled to deliver electrical stimulation using one or more of the vectors found to be suitable.

Figure 15:
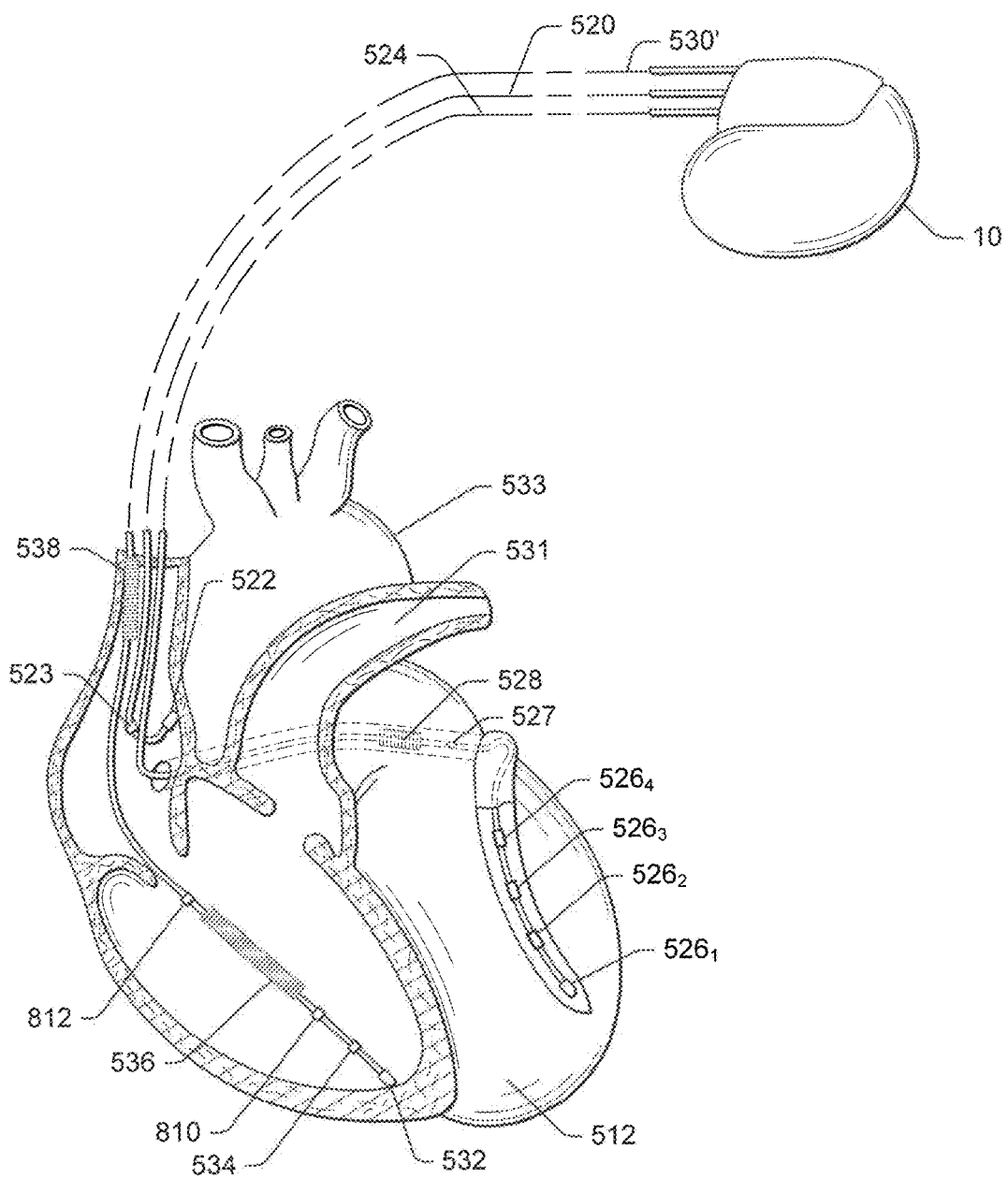
FIG. 15 is a simplified, partly cutaway view, illustrating an alternative implementation of the system of FIG. 1 wherein the RV lead is also a multi-pole lead.

FIG. 15 illustrates a lead system wherein the RV lead is a multi-pole lead, which may be exploited by the method of FIG. 14. Most of the features of the lead system are the same as the system of FIG. 11, described above, except that RV lead 530' is a multi-pole lead. That is, in this example two extra RV ring electrodes are provided (810 and 812) for use in conjunction with electrodes 532 and 534 to provide a quadripolar RV lead. As can be appreciated, more or fewer electrodes may be used and, in some implementations, only the RV lead is multi-polar, in others only the LV lead is multi-polar, and in still other implementations both leads are multipolar (as shown.) The device shown in FIG. 12 can be modified, where appropriate, to include additional electrode terminals and internal components to accommodate the RV multi-pole lead of FIG. 15.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac stimulation device equipped with a right ventricular (RV) lead and a multi-pole left ventricular (LV) lead wherein the device has a programmable set of sensing and stimulation vectors including vectors exploiting lead electrodes as cathodes and vectors exploiting lead electrodes as anodes, the method comprising:
   expediting a test procedure by measuring RV-LV delay times for only a subset of sensing vectors from a total number of possible sensing vectors, wherein each of the sensing vectors in the subset use different electrodes of the LV lead as a sensing cathode and use at least one of a can of the device or an electrode of the RV lead as a sensing anode, wherein the measuring operation includes excluding sensing vectors that use electrodes of the LV lead as sensing anodes;
   selecting an LV electrode based upon a site of latest activation as indicated by the measured delay times from among the LV electrodes used as sensing cathodes to measure the RV-LV delay times;
   measuring a stimulation threshold for at least one stimulation vector that employs the selected LV electrode as a cathode;
   identifying a stimulation vector that employs the selected LV electrode as a cathode and has an acceptable threshold; and
   controlling a pulse generator of the implantable cardiac stimulation device to deliver stimulation using the identified stimulation vector.

2. The method of claim 1 wherein measuring RV-LV delay times includes delivering stimulation pulses using the RV lead and measuring resulting paced RV-LV conduction delay times using a selected LV electrode as a sensing cathode.

3. The method of claim 1 wherein measuring RV-LV delay times includes sensing intrinsic RV activation using the RV lead while sensing intrinsic LV activation using a selected LV electrode as a sensing cathode.

4. The method of claim 1 wherein the acceptable threshold is an acceptable LV capture stimulation threshold.

5. The method of claim 1 wherein the acceptable threshold is an acceptable diaphragmatic stimulation threshold.

6. The method of claim 1 wherein, if none of the stimulation vectors employing the selected LV electrode has an acceptable threshold, then performing the steps of:
   selecting another LV electrode from among the LV electrodes used as sensing cathodes to measure the RV-LV delay times; and
   repeating the steps of measuring thresholds and identifying a stimulation vector that employs the LV electrode as a cathode and has an acceptable threshold.

7. The method of claim 1 wherein at least some of the steps are performed by an external device in communication with the implantable cardiac stimulation device.

8. The method of claim 7 wherein the steps are performed by the external device by transmitting commands to the implantable cardiac stimulation device to control its operation.

9. The method of claim 8 wherein the external device transmits commands to the implantable cardiac stimulation device to control the implantable device to measure the RV-LV delay times and then the external device selects the LV electrode based on the measured delay times as indicated within data received from the implantable device.

10. The method of claim 9 wherein the external device transmits commands to the implantable cardiac stimulation device to control the implantable device to measure the threshold for at least one stimulation vector that employs the selected LV electrode as a cathode and then the external device identifies one or more stimulation vectors that employ the selected LV electrode as a cathode and have acceptable thresholds based on data received from the implantable device.

11. The method of claim 10 wherein the external device transmits commands to the implantable cardiac stimulation device to control the pulse generator of the implantable device to deliver stimulation using one of more of the identified stimulation vectors with the identified LV electrode as a cathode.

12. The method of claim 1 wherein selecting an LV electrode based upon the measured RV-LV delay times is performed to select the LV electrode having a longest RV-LV delay time from among the measured RV-LV delay times.

13. The method of claim 12 wherein, if none of the stimulation vectors employing the selected LV electrode has an acceptable threshold, then performing the steps of:
   selecting the LV electrode having a next longest measured RV-LV delay time; and
   repeating the steps of measuring a stimulation threshold and identifying a stimulation vector that employs the newly-selected LV electrode as a cathode and has an acceptable threshold.

14. The method of claim 1, wherein the LV lead includes at least a proximal electrode, a distal electrode and a mid electrode, the subset including sensing vectors that use each of the proximal electrode, a distal electrode and a mid electrode as the sensing cathode.

15. The method of claim 1, wherein the LV lead includes a plurality of LV electrodes, the sensing vectors in the subset using each of the plurality of LV electrodes as the sensing cathode.

16. An external system for use with an implantable cardiac stimulation device equipped with a right ventricular (RV) lead and a multi-pole left ventricular (LV) lead wherein the device has a programmable set of sensing and stimulation vectors including vectors exploiting lead electrodes as cathodes and vectors exploiting lead electrodes as anodes, the system comprising:

an RV-LV delay time measurement system operative to control the implantable device to expedite a test procedure by measuring RV-LV delay times for only a subset of sensing vectors from a total number of possible sensing vectors, wherein each of the sensing vectors in the subset use different electrodes of the LV lead as a sensing cathode and use at least one of a can of the device or an electrode of the RV lead as a sensing anode, wherein the subset of sensing vectors excludes sensing vectors that use electrodes of the LV lead as sensing anodes;

an LV electrode identification system operative to select an LV electrode based upon a site of latest activation as indicated by the measured delay times from among the LV electrodes used as sensing cathodes to measure the RV-LV delay times;

a stimulation threshold measurement system operative to control the implantable device to measure a stimulation threshold for at least one stimulation vector that employs the selected LV electrode as a cathode;

a vector identification system operative to identify a stimulation vector that employs the selected LV electrode as a cathode and has an acceptable threshold; and a programming controller operative to control the implantable device to deliver stimulation using the identified stimulation vector.

17. An implantable cardiac stimulation device equipped with a right ventricular (RV) lead and a multi-pole left ventricular (LV) lead wherein the device has a programmable set of sensing and stimulation vectors including vectors exploiting lead electrodes as cathodes and vectors exploiting lead electrodes as anodes, the system comprising:

an RV-LV delay time measurement system operative to measure RV-LV delay times for only a subset of sensing vectors from a total number of possible sensing vectors, wherein each of the sensing vectors in the subset use different electrodes of the LV lead as a sensing cathode and use at least one of a can of the device or an electrode of the RV lead as a sensing anode, wherein the subset of sensing vectors excludes sensing vectors that use electrodes of the LV lead as sensing anodes;

an LV electrode identification system operative to select an LV electrode based upon a site of latest activation as indicated by the measured delay times from among the LV electrodes used as sensing cathodes to measure the RV-LV delay times;

a stimulation threshold measurement system operative to measure a stimulation threshold for at least one stimulation vector that employs the selected LV electrode as a cathode;

an LV-based vector selection system operative to identify a stimulation vector that employs the selected LV electrode as a cathode and has an acceptable threshold; and a controller operative to deliver stimulation using the identified stimulation vector.

18. A system for use with an implantable cardiac stimulation device equipped with a right ventricular (RV) lead and a multi-pole left ventricular (LV) lead wherein the device has a programmable set of sensing and stimulation vectors including vectors exploiting lead electrodes as cathodes and vectors exploiting lead electrodes as anodes, the system comprising:

means for measuring RV-LV delay times for only a subset of sensing vectors from a total number of possible sensing vectors, wherein each of the sensing vectors in the subset use different electrodes of the LV lead as a sensing cathode and use at least one of a can of the device or an electrode of the RV lead as a sensing anode, wherein the subset of sensing vectors excludes sensing vectors that use electrodes of the LV lead as sensing anodes;

means for selecting an LV electrode based upon a site of latest activation as indicated by the measured delay times from among the LV electrodes used as sensing cathodes to measure the RV-LV delay times;

means for measuring a stimulation threshold for at least one stimulation vector that employs the selected LV electrode as a cathode;

means for identifying a stimulation vector that employs the selected LV electrode as a cathode and has an acceptable threshold; and means for controlling a pulse generator of the implantable cardiac stimulation device to deliver stimulation using the identified stimulation vector.

* * * * *